(12) United States Patent
Russo

(10) Patent No.: US 11,185,317 B2
(45) Date of Patent: Nov. 30, 2021

(54) MEDICAL ADHESIVE APPLICATOR

(71) Applicant: Rousseau Research, Inc., Palo Alto, CA (US)

(72) Inventor: Joseph D. Russo, Palo Alto, CA (US)

(73) Assignee: Rousseau Research, Inc., Palo Alto, CA (US)

( * ) Notice: Subject to any disclaimer, the term of this patent is extended or adjusted under 35 U.S.C. 154(b) by 0 days.

(21) Appl. No.: 17/204,775

(22) Filed: Mar. 17, 2021

(65) Prior Publication Data

US 2021/0196254 A1 Jul. 1, 2021

Related U.S. Application Data

(63) Continuation-in-part of application No. 16/686,015, filed on Nov. 15, 2019, which is a continuation of
(Continued)

(51) Int. Cl.
| | |
|---|---|
| *B43K 5/14* | (2006.01) |
| *A61B 17/00* | (2006.01) |
| *B05D 1/26* | (2006.01) |
| *A61M 35/00* | (2006.01) |
| *A61F 13/40* | (2006.01) |

(Continued)

(52) U.S. Cl.
CPC ..... *A61B 17/00491* (2013.01); *A61M 35/003* (2013.01); *A61M 35/006* (2013.01); *B05C 17/00583* (2013.01); *B05C 17/00586* (2013.01); *B05D 1/26* (2013.01); *A61B 2017/00495* (2013.01); *A61B 2017/00884* (2013.01); *A61B 2050/314* (2016.02); *A61B 2090/037* (2016.02); *B05C 17/002* (2013.01); *B05C 17/00553* (2013.01); *B05D 1/34* (2013.01)

(58) Field of Classification Search
CPC ...... A61B 17/000491; B05C 17/00583; B05C 17/00586; B05D 1/26; A61M 35/003; A61M 35/006
USPC .................................................. 401/23, 183
See application file for complete search history.

(56) References Cited

U.S. PATENT DOCUMENTS

| | | | |
|---|---|---|---|
| 6,202,897 B1 * | 3/2001 | Martin .............. | B05C 17/00593 206/269 |
| 6,283,933 B1 * | 9/2001 | D'Alessio .......... | A61M 35/003 401/132 |

(Continued)

*Primary Examiner* — Jennifer C Chiang
(74) *Attorney, Agent, or Firm* — Dergosits & Noah LLP; Michael E. Dergosits

(57) ABSTRACT

Medical adhesive applicators are disclosed which allow medical adhesives to have long storage life and be easily dispensed in a controlled manner. In one embodiment, the applicator has a frangible glass vial with the medical adhesive. The frangible glass vial is held in a plastic enclosure with a dispensing tip. Attached to the plastic enclosure is a squeeze tube capable of imparting air pressure into the enclosure. In another embodiment, the applicator has a proximal chamber containing medical adhesive, a distal chamber for dispensing medical adhesive and one or more rupturable membranes between them. In another embodiment, an applicator pad is sized to retain the total volume of adhesive and initiator so that, in use, the entire volume of adhesive liquid is first loaded into the pad. So loaded, the adhesive and initiator mix evenly to provide an adhesive layer that cures puddle-free.

20 Claims, 23 Drawing Sheets

Related U.S. Application Data application No. 15/944,648, filed on Apr. 3, 2018, now Pat. No. 10,478,167.

(60) Provisional application No. 62/566,217, filed on Sep. 29, 2017.

(51) Int. Cl.
*B05C 17/005* (2006.01)
*B05D 1/34* (2006.01)
*A61B 50/30* (2016.01)
*A61B 90/00* (2016.01)
*B05C 17/00* (2006.01)

(56) References Cited

U.S. PATENT DOCUMENTS

| | | | |
|---|---|---|---|
| 6,439,789 B1 * | 8/2002 | Ballance | A61B 17/00491 401/134 |
| 6,595,940 B1 * | 7/2003 | D'Alessio | A61M 35/003 604/3 |
| 8,550,737 B2 * | 10/2013 | Ruiz, Sr. | A61B 17/00491 401/134 |
| 9,066,711 B2 * | 6/2015 | Ruiz, Sr. | A46B 11/0075 |
| 9,877,709 B2 * | 1/2018 | Ruiz, Sr. | A46B 11/0075 |

* cited by examiner

MEDICAL ADHESIVE APPLICATOR

CROSS-REFERENCES TO RELATED APPLICATIONS

This application is a Continuation-in-Part of U.S. patent application of U.S. patent application Ser. No. 16/686,015, filed on Nov. 15, 2019; which is a continuation of U.S. patent application Ser. No. 15/944,648, filed on Apr. 3, 2018, now U.S. Pat. No. 10,478,167, issued on Nov. 19, 2019; which in turn claims priority to U.S. Provisional Patent Application No. 62/566,217, filed Sep. 29, 2017, all entitled "Medical Adhesive Applicator," the disclosure of each of which is incorporated by reference in its entirety for all purposes.

FIELD OF THE INVENTION

The present invention pertains to improved disposable applicators for dispensing fluid compositions, especially medical adhesive compositions.

BACKGROUND OF THE INVENTION

In medicine, adhesives are needed for many different purposes, including liquid bandages, wound dressings, skin bonding surgical adhesives, sealants, bioactive release matrixes and implants. Because of the need for sterility in medicine, most medical adhesives are applied from single use adhesive applicators. A popular medical adhesive in a single use applicator is the DERMABOND® medical adhesive developed by Closure Medical Corporation and now sold by Ethicon, a subsidiary of Johnson & Johnson Corporation. As illustrated in FIG. 1 and also described in U.S. Pat. Nos. 5,928,611; 6,099,807 and 6,676,322, an applicator 10 used for the DERMABOND® medical adhesive includes a frangible glass vial 14 held inside a plastic enclosure 16. The primary reasons a frangible glass ampoule is used is to provide in inert storage compartment, which increases the stability of the cyanoacrylate adhesive, and to maintain the cyanoacrylate separately from a polymerizing initiator until time of use. At the dispensing end of the DERMABOND® plastic enclosure is an applicator tip with a porous plug 18. The porous plug 18 is infused with an accelerator/initiator for accelerating the curing of the DERMABOND® cyanoacrylate adhesive 12. To release the adhesive, one presses on the DERMABOND® plastic enclosure with enough strength to break the frangible glass vial 14. When the frangible glass vial 14 is broken, adhesive slowly flows out of the cracked vial through capillary action and onto the porous plug 18 of the applicator tip. The adhesive can only flow through the porous plug by repetitive squeezing of the plastic enclosure 16. Eventually, the adhesive can be squeezed through the porous plug 18 and applied to the medical use (e.g., sealing a wound). To increase flow rates from squeezing, the DERMABOND® porous tip has been replaced in newer versions with an applicator tip having a porous wafer and a longitudinal hole or lumen. Nonetheless, repetitive squeezing of the plastic enclosure is also required to push adhesive through the porous wafer and longitudinal hole or lumen.

While the DERMABOND® system is in widespread use, it has a number of significant disadvantages. For example, when the DERMABOND® glass vial is crushed, glass shards are created. These glass shards can build up on the porous plug applicator tip. Such a shard build-up can greatly impede the flow of medical adhesive past the build-up. Where the porous plug is replaced by an applicator tip having a longitudinal hole or lumen, the flow of adhesive is increased but so is the possibility of glass shards coming out of the applicator. Obviously, mixing glass shards with medical adhesive is dangerous. Moreover, the flow of adhesive in the DERMABOND® system is difficult to control due to the pressure needed to force the adhesive through the applicator tip. While one can vigorously press on the DERMABOND® plastic enclosure, the DERMABOND® applicator design fails to create a strong, constant force for the adhesive flow. Typically, the adhesive will come out slowly or in spurts—neither of which is desirable in a medical setting where dispensing in a carefully controlled manner is of critical importance. Further, a DERMABOND®-type applicator has a tendency to introduce bubbles into the medical adhesive being dispensed. In adhesives having a water-like viscosity, this is not a big issue because the bubbles tend to break upon emanating from the dispenser tip. However, this is not true for more viscous adhesives, such as the cyanoacrylates used in DERMABOND®, which are activated in the porous plug and, consequently, whose viscosity is already increasing as they are being dispensed. A further failing of cyanoacrylate applicators that employ glass ampoule vials is that dispensing requires the co-elution of the cyanoacrylate liquid with the initiator contained in the dense porous plug or dense porous wafer. Unfortunately, the initial flowthrough of liquid picks up a larger dose of initiator than subsequent flowthrough until finally little or no initiator remains. This "wash out" effect results in non-uniform and thus different cure rates. On skin protectant applications the non-uniform results can lead to very slow or non-curing puddles, caused by initiator being deficient in proportion to the adhesive applied. The health care provider's time is thusly negatively impacted. As a safety issue, the need to crush a glass ampoule creates a danger to health care providers by creating glass shards. Also, it is known that many healthcare providers find it physically challenging to crush the glass ampoules.

A form of fluid dispenser is disclosed in May's U.S. Pat. No. 6,641,319 ("May patent"), the disclosure of which is hereby incorporated by reference. Rather than using a glass vial within a plastic enclosure to hold fluid as is done in the DERMABOND® applicator, the May patent creates two chambers in a single plastic enclosure. May's proximal chamber is used to hold unused fluid while May's distal chamber is used to dispense fluid. To separate the two chambers, May places a rupturable membrane between the two chambers in the form of a circular disk with a series of molded radial depressions or weld seams extending from a center point of the disk. When one wants to dispense adhesive from the May applicator, one presses on the outside of May's rupturable membrane until it cracks open and allows fluid to flow from May's proximal chamber to May's distal chamber. With May's membrane ruptured, continued squeezing of May's proximal chamber forces adhesive into May's distal, dispensing chamber and then out of May's applicator altogether.

Even if May's dispenser were used for medical adhesive purposes, May's dispenser would have problems for this application, particularly for cyanoacrylate medical adhesives. Cyanoacrylate monomer compositions, such as those described in Hickey's U.S. Pat. No. 6,743,858, are liquid compositions of monomer that behave like solvents and permeate as well as chemically attack blow molded plastic enclosures made of low-density polyethylene ("LDPE"), mixtures of LDPE and high-density polyethylene ("HDPE"), polypropylene and/or other resins and thus lack the ability to age properly in these containers. The permeation and container wall attack reaction cause the adhesives to polymerize as they age in an applicator made from this group of plastics. By comparison, no permeation occurs in the type of borosilicate glass used in the DERMABOND® frangible glass vials. Due to this permeation and container wall attack in the May dual chamber applicator, cyanoacrylate adhesives typically solidify in several months or earlier in the type of applicator disclosed in May's patent.

Accordingly, there is a need for a medical adhesive applicator where the medical adhesive can be easily dispensed in a controlled manner. There is also a need for a medical adhesive applicator for cyanoacrylate medical adhesives which allows the medical adhesives to not only be easily dispensed but also have a long shelf life. There is also a need for a medical cyanoacrylate adhesive and skin sealant applicator that eliminates the need for glass ampoules and that provides a thoroughly and uniformly initiated cyanoacrylate.

BRIEF SUMMARY OF THE INVENTION

In one preferred embodiment, the present invention adds a squeeze tube to a conventional type of frangible glass vial and plastic enclosure applicator design, such as that used in the popular DERMABOND® commercial product. The squeeze tube preferably has a neck to seal (e.g., including compression fit, with adhesive, with sealant etc.) around the outside of the plastic enclosure and a bellows section. To allow the squeeze tube of the present invention to easily apply pneumatic pressure to force out adhesive, an aperture is formed at or near the proximal end of the enclosure.

To operate the squeeze tube applicator of the present invention, one begins by pressing the sides of the plastic enclosure in a conventional way to crush the frangible glass vial contained in the plastic enclosure. As the adhesive begins to slowly flow out of the broken glass vial, one then presses on the bellows portion of the squeeze tube to impart pneumatic pressure through the aperture in the enclosure to push adhesive out of the applicator tip. Because of the pneumatic pressure generated by the squeeze tube, the squeeze tube applicator of the present invention can be easily used with porous plug applicator tips which block glass shards from passing out of the applicator. If desired, the squeeze tube applicator of the present invention can also be used with an applicator tip having porous wafer and a longitudinal hole or lumen.

In a second preferred embodiment, a dual chamber applicator is used. As in the May patent, a preferred form of dual chamber applicator has a proximal chamber for holding adhesive, a distal chamber for dispensing adhesive and one or more rupturable membranes between the two chambers in the form of a circular disk(s) with a series of molded radial depressions or weld seams extending from a center point of the disk(s). Unlike May's dual chamber applicator, the plastic used to form the dual chamber applicator of the present invention is fluorinated. This fluorinated plastic allows adhesives in the dual chamber applicator of the present invention, particularly cyanoacrylate adhesives, to have long shelf lives. In the second preferred embodiment, the fluorination preferably takes place when the applicator plastic is formed or when the dual chamber applicator is blow molded. As in the first preferred embodiment, either porous plug applicator tips or applicator tips having a porous wafer with a longitudinal hole or lumen can be used with the dual chamber applicator.

In a third preferred embodiment, a squeezable fluorinated polymer vial sealed chamber is used to provide storage stability. At the time of use the cap on said vial is removed by unscrewing or pulling, if it is a pressure fitted cap, from the top of the sealed chamber vial, then discarding it. The cap is replaced with an open cell foam head valve dispenser cap. When the vial thusly capped is inverted, squeezing the vial easily causes liquid to flow into the open cell foam head dispensing cap, allowing the adhesive (or sealant) fluid to be loaded into the foam head where it fully mixes with the initiator (or accelerator) that resides in the interstices and surfaces of the open cell foam. Thus, when the initiated sealant or wound adhesive is applied to skin or an incision wound it is uniformly mixed and therefore cures uniformly. Also, unlike glass ampoule applicators, in the third embodiment the applicator parts are recyclable. Generally, the third embodiment, and similar embodiments in which glass is not used as the vial material, have the advantages of two years plus storage stability, an increased number of vial volume choices (vials from a few milliliters to several milliliters), and uniformly initiated/accelerated adhesive/sealant, even when providing a feather-light transfer of adhesive to the application surface.

BRIEF DESCRIPTION OF THE DRAWINGS

The embodiments are illustrated by way of example and not limitation in the accompanying drawings, in which like references indicate similar elements, and in which.

DETAILED DESCRIPTION

Figure 2:
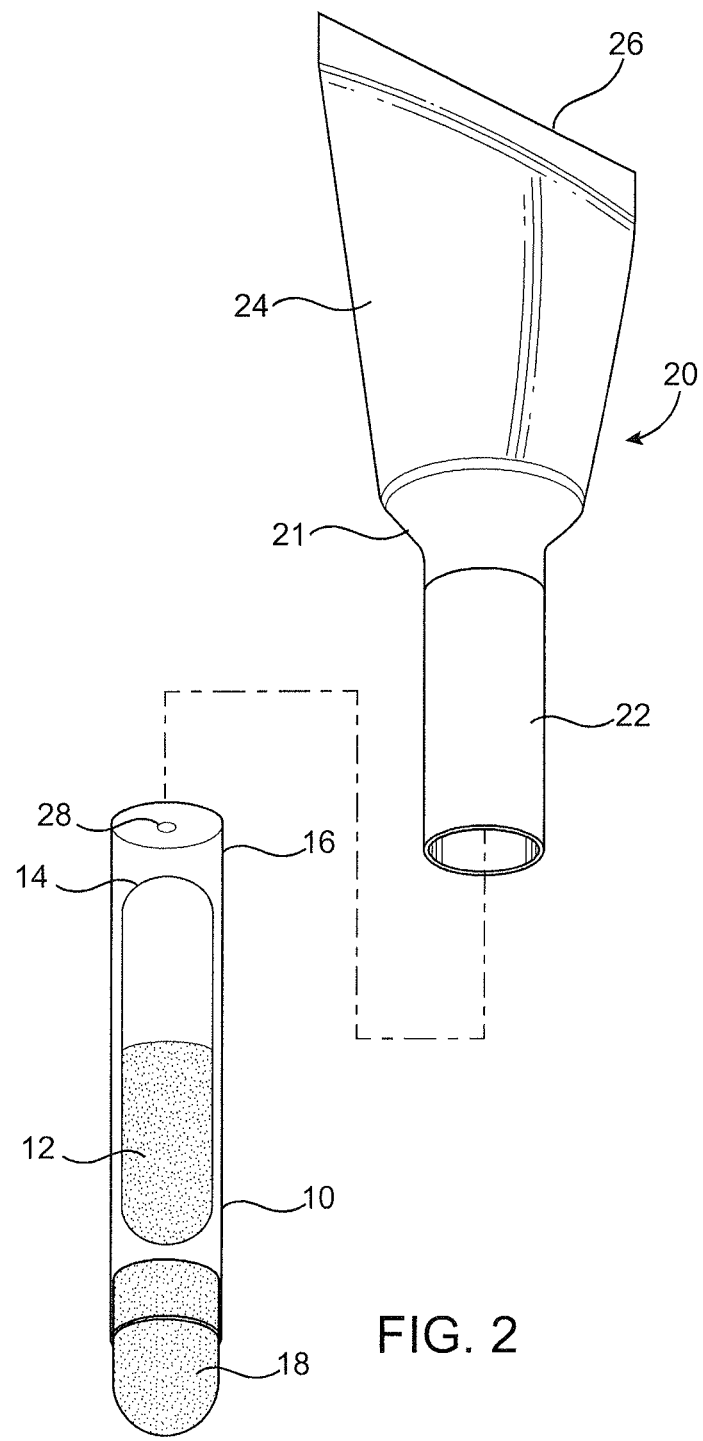
FIG. 2 is an exploded view of a first preferred embodiment where a squeeze tube is added to a modified form of a conventional frangible glass medical adhesive applicator.
Figure 3:
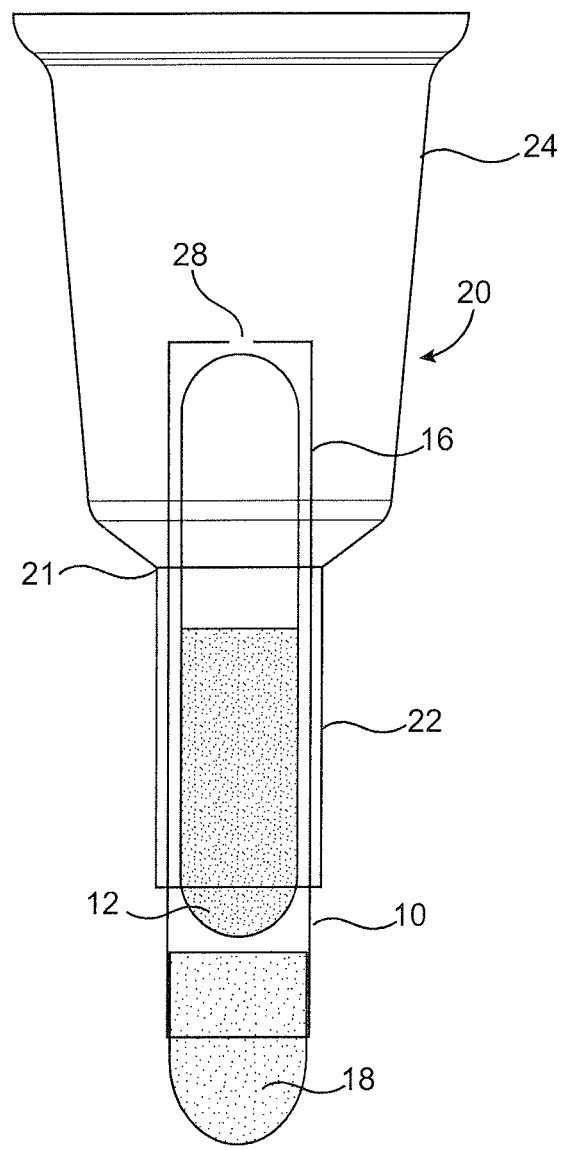
FIG. 3 is an assembled view of the FIG. 2 applicator.

Referring now to FIGS. 2 and 3, a preferred form of squeeze tube applicator 20 of the present invention is shown. In this preferred embodiment, a conventional DERMABOND®-style applicator 10 forms part of the applicator 20 of the present invention. The DERMABOND®-style applicator 10 includes a frangible glass vial 14 holding an adhesive compound 12, a generally cylindrical plastic enclosure 16 holding the frangible glass vial 14 and a porous plug 18. The porous plug 18 is preferably infused with an accelerator and/or initiator for accelerating the curing of adhesive compound 12.

To allow adhesive to be dispensed easily and in a controlled manner, a squeeze tube 21 is added to the DERMABOND®-style applicator 10. The squeeze tube 21 preferably has a proximal bellows portion 24 and a distal neck portion 22. The bellows portion 24 acts like a balloon to store air and allow it to be easily pushed out of the squeeze tube 21. The squeeze tube 21 is preferably made of a flexible plastic. Where the bellows portion 21 is blow molded, it can be sealed by crimping its proximal end 26. The distal neck portion 22 is sized to fit snugly around the outside surface of the plastic enclosure 16 as shown in FIG. 3. This snug, sealing fit can be accomplished by, among other things, a compression fit, with adhesive or with sealant. Where the DERMABOND®-style applicator's plastic enclosure 16 is generally cylindrical in shape, the distal neck portion 22 of the squeeze tube 21 would also be generally cylindrical in shape (but of a slightly larger internal diameter). The objective is to create an air tight seal between the distal neck portion 22 of the squeeze tube 21 and the outside surface of the plastic enclosure 16. To funnel pneumatic pressure from the squeeze tube 21 into the interior of the plastic enclosure 16, an aperture 28 is formed at or about the proximal end of the of the plastic enclosure 16.

As those of skill in the art will recognize, the enclosure 16 of the squeeze tube applicator 20 can have many different shapes, including elliptical, rectangular, square and hexagonal cross-sectional shapes. What is important is that the distal neck portion 22 of the squeeze tube 21 be able to conform to the shape of the enclosure 16 to create an air-tight seal so that the pneumatic pressure created by the bellows portion 24 of the squeeze tube 21 can be focused into the aperture 28 in the enclosure rather than being dissipated. Similarly, while the squeeze tube applicator 20 of the present invention is particularly advantageous for dispensing medical adhesives, such as 2-octyl cyanoacrylates or formulated 2-octyl cyanoacrylates, those of skill in the art will recognize that the squeeze tube applicator 20 of the present invention could also be used for dispensing many other types of fluids.

Figure 4:
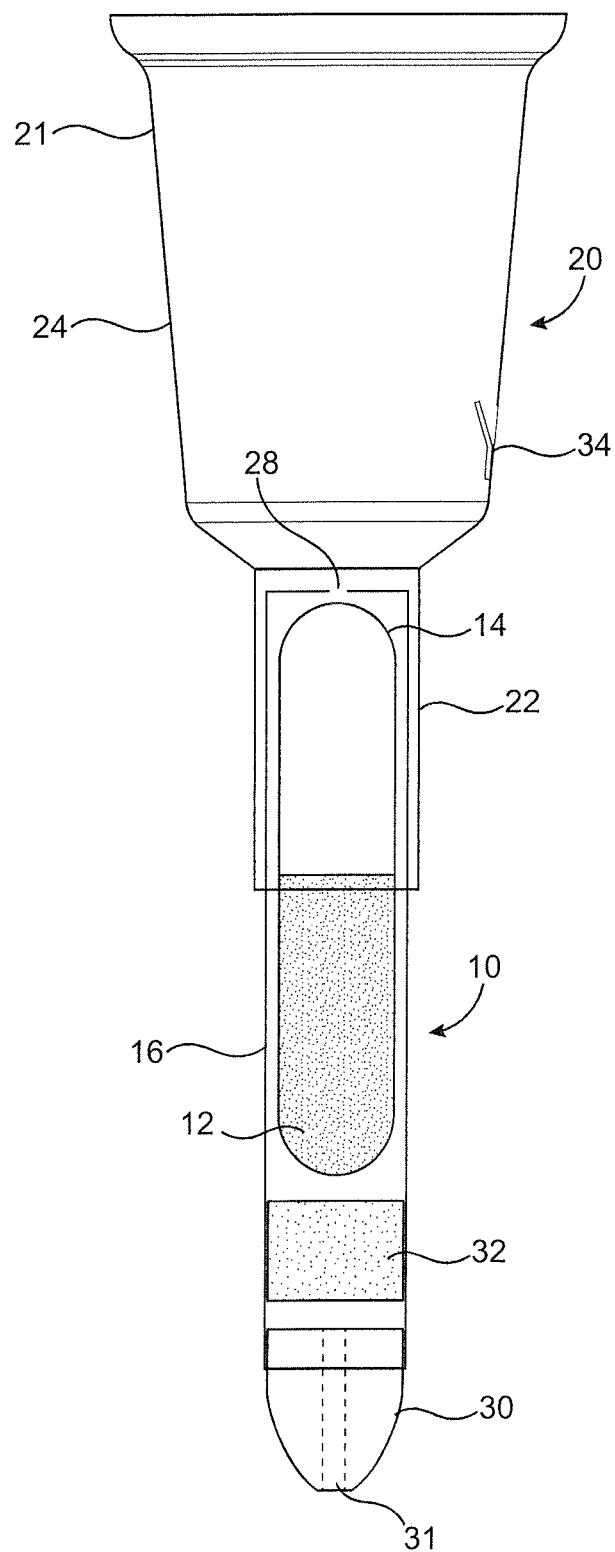
FIG. 4 is an assembled view of a squeeze tube applicator with a longitudinal hole applicator tip and a one-way valve in the bellows portion of the squeeze tube.

FIG. 4 illustrates a modified squeeze tube applicator 20 embodiment. Rather than having a porous plug at the distal end of the enclosure 16, FIG. 4 shows that an applicator tip 30 with a longitudinal hole or lumen 31 placed at the distal end of the enclosure 16 to facilitate adhesive flow. In this embodiment, a porous wafer 32 would preferably be placed above the applicator tip 30 to allow accelerator/initiator to be co-eluted with the adhesive 12 before the adhesive 12 exits through the applicator tip 30 and to help prevent glass shards from the frangible glass vial 14 from passing through the applicator tip 30. FIG. 4 also illustrates that a one-way valve 34 can be placed in the bellows portion 24 of the squeeze tube 21. This one-way valve 34 allows the bellows portion 24 of the squeeze tube 21 to quickly refill with air after it is initially squeezed while preventing air from escaping.

Figure 5:
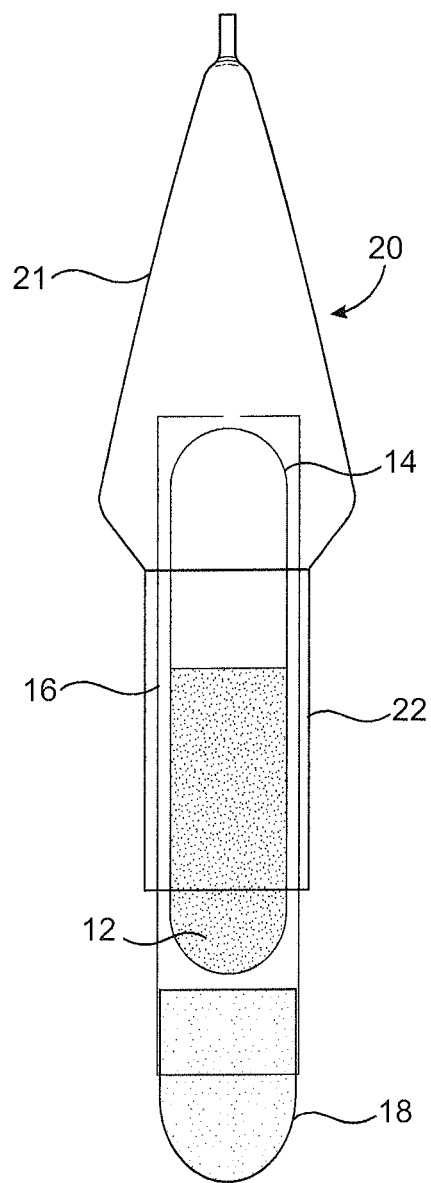
FIG. 5 illustrates the squeeze tube applicator of FIG. 3 prior to use.
Figure 6:
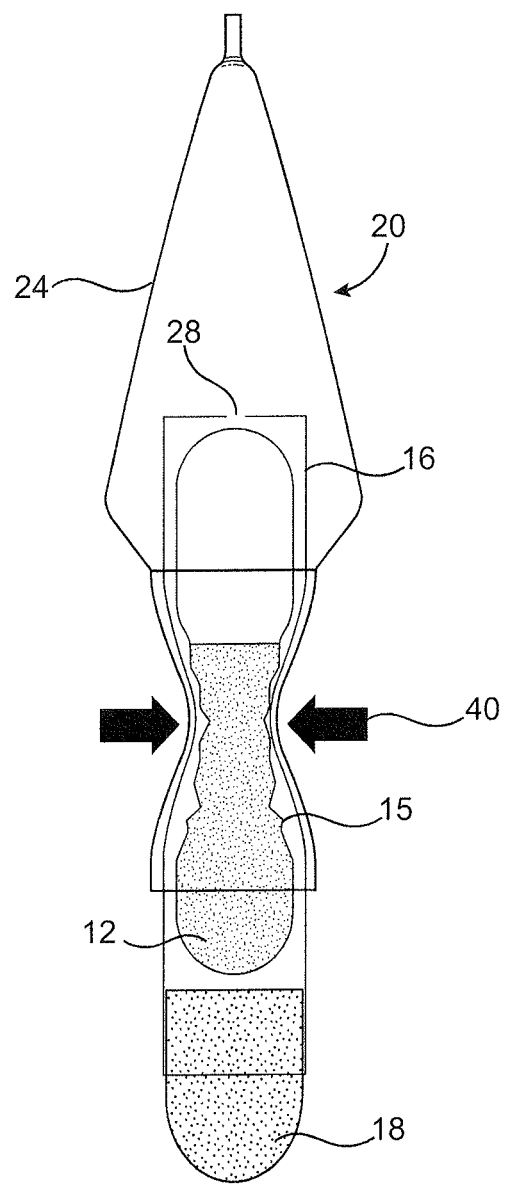
FIG. 6 illustrates pressure applied to the plastic enclosure of the FIG. 3 applicator to break the frangible glass vial.
Figure 7:
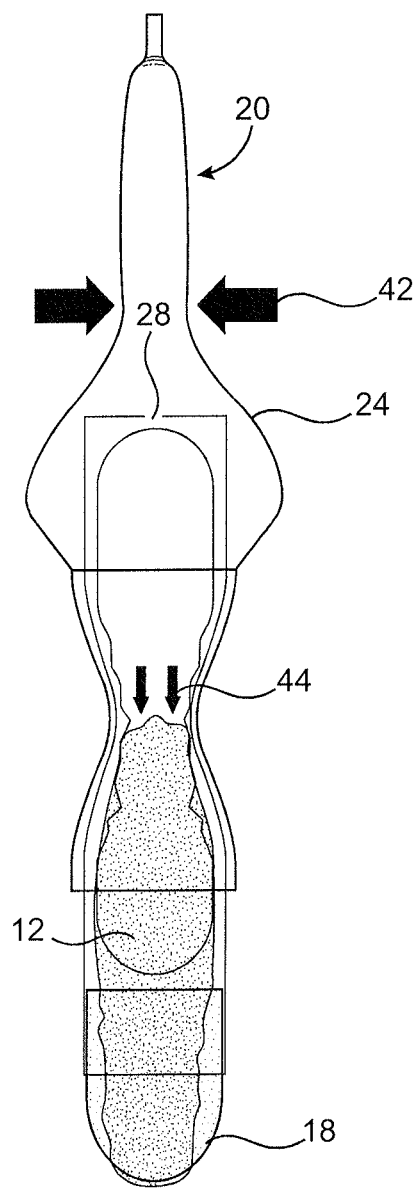
FIG. 7 illustrates how squeezing the squeeze tube of the FIG. 3 applicator creates pneumatic force to drive adhesive out of the broken glass vial and toward the applicator tip.
Figure 8:
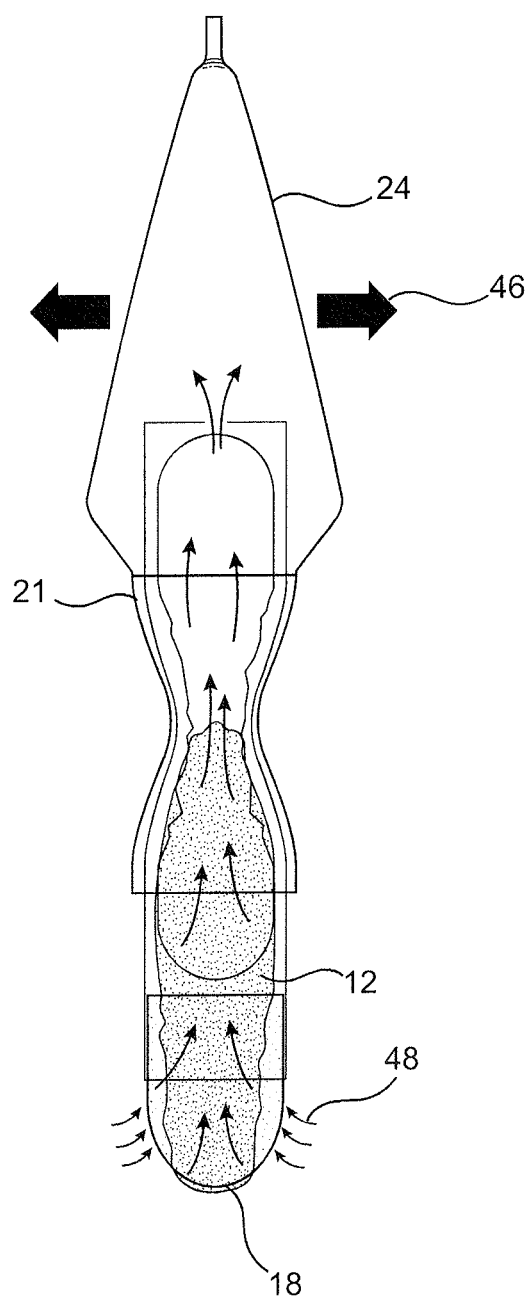
FIG. 8 illustrates how air is pulled back into the FIG. 3 squeeze tube as pressure on the squeeze tube is released.
Figure 9:
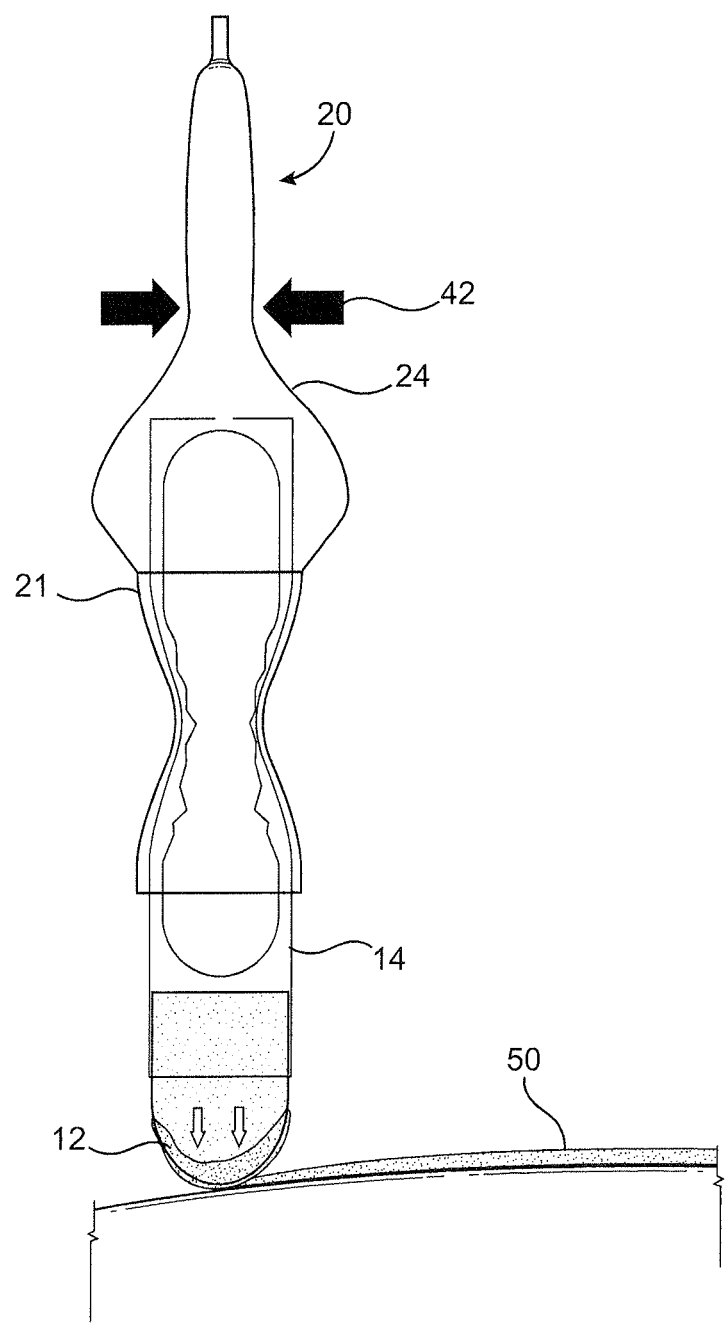
FIG. 9 illustrates how squeezing the squeeze tube of the FIG. 3 applicator a second time forces additional adhesive out of the enclosure.

FIGS. 5-9 illustrate how the squeeze tube applicator 20 of the present invention can be used with very little effort to dispense medical adhesive in a carefully controlled manner. FIG. 5 illustrates the squeeze tube applicator 20 prior to use. The adhesive 12 is stored in a sealed glass vial 14 enclosed within a plastic enclosure 16. At the proximal end of the plastic enclosure 16 is the squeeze tube 21 and at the distal end is a porous plug 18 with accelerator/initiator. As shown in FIG. 6, one releases adhesive 12 from the squeeze tube applicator 20 by first applying simultaneous pressure 40 on the sides of the neck portion 22 of the squeeze tube 21 and enclosure 16 adjacent to the frangible glass vial 14. This pressure 40 is typically provided by the user's fingertips. When sufficient pressure 40 is applied to break the glass vial 14, adhesive 12 flows out of the broken vial and into the plastic enclosure 16. To easily move the adhesive 12 down into the porous plug 18 in a controlled manner, pressure 42 should next be applied to the bellows portion 24 of the squeeze tube 21 as shown in FIG. 7. Again, pressure 42 is typically applied by the user's fingertips. When the bellows portion 24 of the squeeze tube 21 is squeezed in this way, firm air pressure 44 is channeled through aperture 28 and onto the surface of the adhesive 12 in a way that pushes the adhesive 12 into the porous plug 18. Referring now to FIG. 8, when one releases pressure 46 from the bellows portion 24 of the squeeze tube 21, air is drawn 48 into the squeeze tube 21 through the porous plug 18 to refill the bellows portion 24 of the squeeze tube 21 as air flows through the aperture 28. As shown in FIG. 9, with a minimum of additional squeezes 42 of the bellows portion 24 of the squeeze tube 21, once can push out additional adhesive 12 from the plastic enclosure 16 onto the applicator surface 50.

In the prior art DERMABOND® applicator, one had to try to generate pressure by continually pressing on the sides of the plastic enclosure adjacent to the broken glass vial. Most conventional enclosures contain less than approximately 1 ml. volume of air to dispense the liquid. The present invention increases the pneumatic pressure by several times more than conventional applicators. The ingress of air to reload the squeeze tube 21 pressure is enhanced by the volume of liquid displacement in dispensing, giving extremely fine precision control to the user. A 5 ml. applicator, made thusly, dispenses the liquid with great ease, giving the user precision control heretofore unknown in the art. This precision is very valuable to surgeons or medical practitioners. Glass shards which may have blocked flow in a DERMABOND®-style applicator are no longer an impediment to dispensing. Bubbles collapse easily under the higher pressure.

Figure 10:
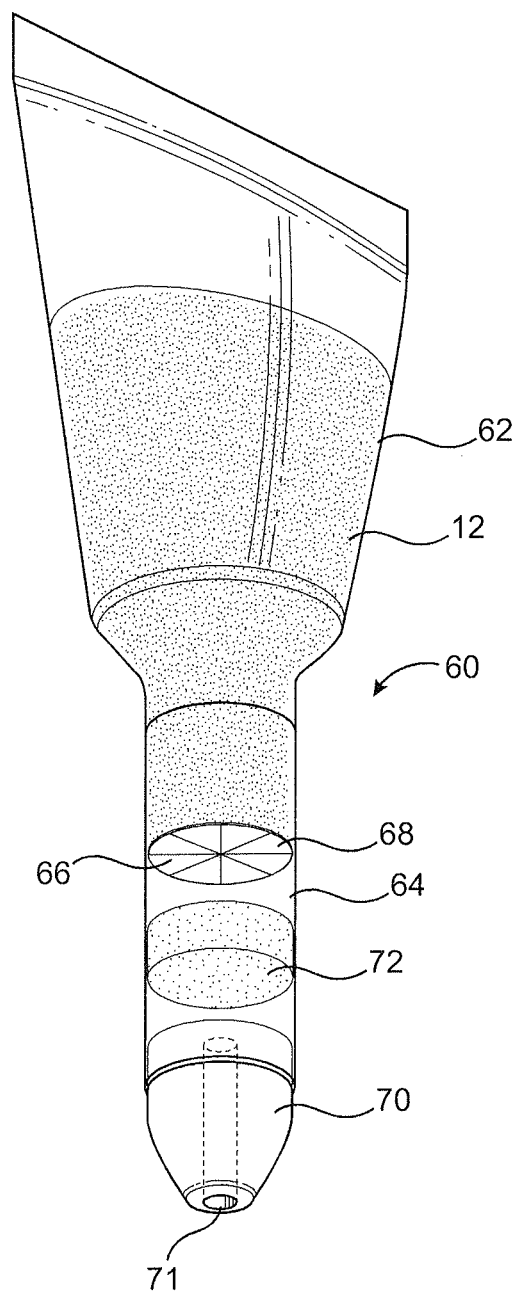
FIG. 10 illustrates a dual chamber adhesive applicator with fluorinated plastic, a rupturable membrane and an applicator tip having a longitudinal hole.
Figure 11:
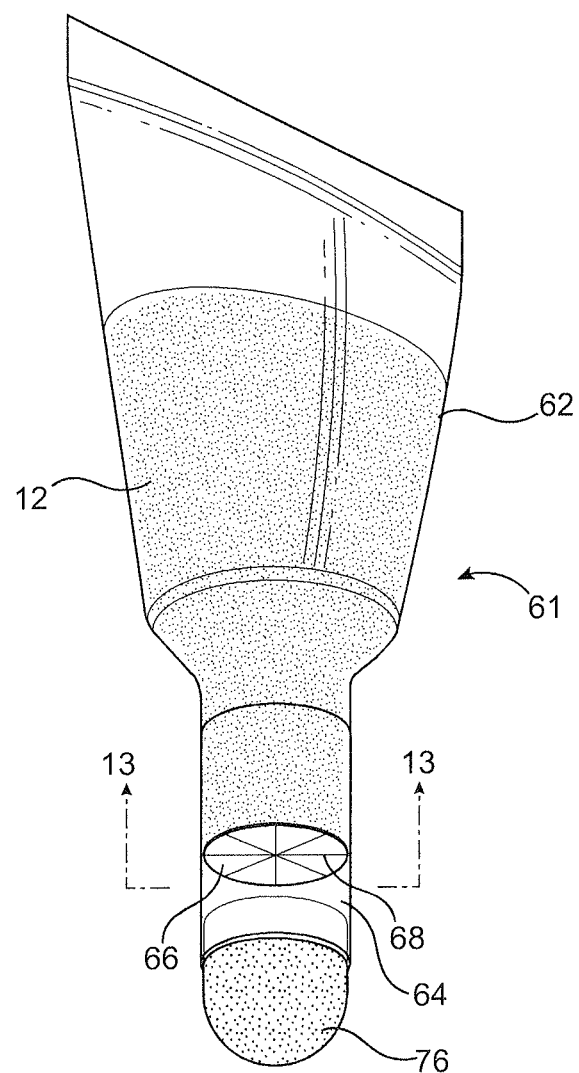
FIG. 11 illustrates a dual chamber adhesive applicator with fluorinated plastic, a rupturable membrane and a porous plug applicator tip.

Referring now to FIGS. 10 and 11, further preferred applicator 60, 61 embodiments are shown. These forms of applicators 60, 61 avoid use of a frangible glass vial and the broken shards of glass associated with such a vial. These alternative applicators 60, 61 are preferably formed from plastic and have two chambers, a proximal chamber 62 to hold adhesive and a distal chamber 64 to dispense adhesive. An applicator tip 70 with a longitudinal hole or lumen 71 can be placed at the end of the distal chamber 64 as shown in FIG. 10 or a porous plug applicator tip 76 can be placed at the end of the distal chamber as shown in FIG. 11. Where the applicator tip 70 with the longitudinal hole or lumen 71 is used, a porous wafer 72 with accelerator/initiator can advantageously be placed between the adhesive 12 and the applicator tip 70 to activate the adhesive during the dispensing process. During manufacture, the two chambers 62, 64 can be formed by a blow molded process. The applicator tip 70, 76 can be inserted by compression fit or by being adhered, heat sealed or solvent welded.

Figure 12:
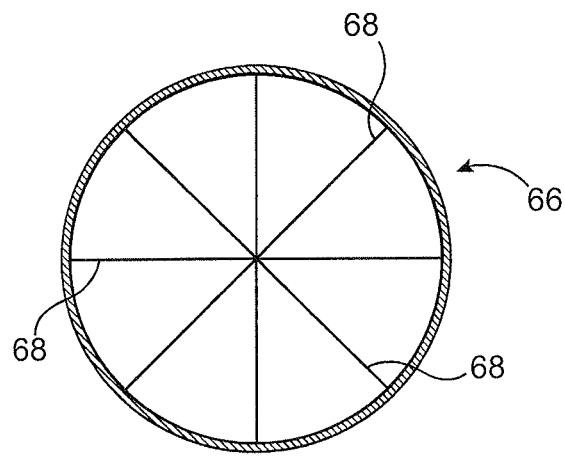
FIG. 12 shows a close-up view of the rupturable membrane of the FIG. 10 applicator prior to the membrane's rupture.
Figure 13:
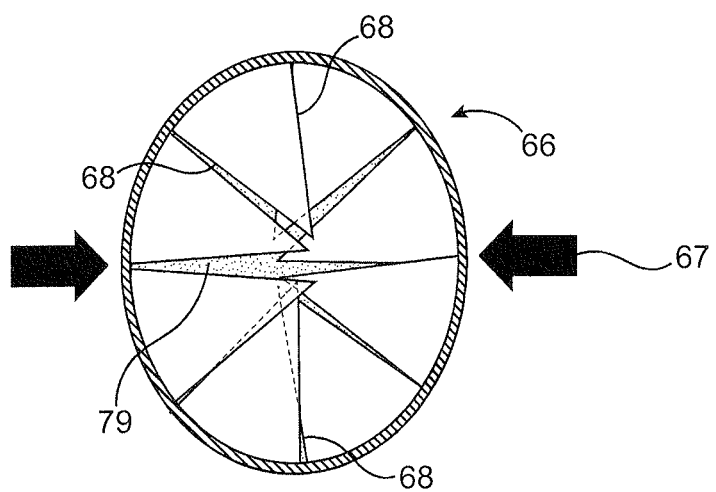
FIG. 13 shows a close-up view of the rupturable membrane of the FIG. 10 aperture after the membrane has been ruptured.

In the FIGS. 10 and 11 embodiments, the two chambers 60, 64 are separated by one or more rupturable membranes 66, preferably in the form of a circular disk scored with a series of molded radial depressions or weld seams 68. Before use, the rupturable membrane(s) 66 acts as an impermeable barrier which holds the adhesive in the proximal chamber 62 and prevents it from moving into the distal chamber 64. A close-up view of a rupturable membrane 66 before use is shown in FIG. 12. Further details about suitable types of rupturable membranes for the present invention are provided in May's U.S. Pat. No. 6,641,219. To allow adhesive to be dispensed from applicators 60, 61, one applies pressure 67 to the sides of the rupturable membrane(s) 66 as shown in FIG. 13. When sufficient pressure is applied, the circular disc 66 ruptures along one or more of the molded radial depressions or weld seams which creates gaps 79 for adhesive 12 to flow from the proximal chamber 62 to the distal chamber 64 and ultimately, after applying further pressure to the sides of the proximal chamber 62, through to the applicator tip 70, 76. By using more than one rupturable membrane 66, one can create a stronger barrier to protect against detrimental permeation and accidental release of adhesive where one of the rupturable barriers is inadvertently damaged or otherwise compromised.

As compared with the FIGS. 1-9 applicator embodiments, the FIGS. 10-13 applicator embodiments have the advantage of being able to hold more adhesive in a comparably sized applicator. A DERMABOND®-style applicator, such as the one illustrated in FIG. 1, typically carries 0.36 to 0.8 ml. of adhesives, enough to cover small incisions or wounds. The increased volume of the rupturable membrane applicators illustrated in FIGS. 10-13 allows for packaging larger volumes of liquid adhesive, thereby making it possible to cover greater area on any substrate. For example, at a higher volume of 2-5 ml. or more, a medical practitioner can cover longer incisions or larger wounds, such as ulcers. Using 2-octyl cyanoacrylate or formulated 2-octyl cyanoacrylate adhesive, an ulcer treatment can be accomplished by barrier sealing ulcers at weekly intervals in place of the more repetitive, expensive daily protocols presently in use.

Where the applicators 60, 61 illustrated in FIGS. 10-13 are formed from the types of plastics that are commonly used for such applicators, such as low-density polyethylene ("LDPE"), mixtures of LDPE and high-density polyethylene ("HDPE"), polypropylene and/or similar resins, problems can develop if those applicators are filled with cyanoacrylate monomer adhesives, such as 2-octyl cyanoacrylate. Cyanoacrylate monomer adhesives, such as those described in Hickey's U.S. Pat. No. 6,743,858, are liquid compositions of monomer that behave like solvents and permeate as well as chemically attack the plastic applicators. The cyanoacrylate adhesives thus lack the ability to age properly in these applicators. The permeation and container wall attack reaction cause the adhesives to polymerize as they age in such applicators.

To overcome this aging problem, the plastic applicators 60, 61 illustrated in FIGS. 10-13 are fluorinated. Fluorinating plastics renders them resistant to permeation by replacing hydrogen atoms in the plastic container surfaces with larger fluorine atoms, thereby creating a barrier. Companies that commercially fluorinate plastics include Fluoro-Seal Corp., Houston, Tex. and their licensee, Betix, Ltd., Bolton, UK. The fluorination preferably takes place when the applicator plastic is formed or when the dual chamber applicator is blow molded. The fluorinating process provides the long shelf life stability desired for applicators holding 2-octyl cyanoacrylate adhesives. Morales U.S. Published Patent Application No. 2008/0311323, which is hereby incorporated by reference, recognizes the value of using fluorinated plastics in connection with cyanoacrylate compounds. Fluorinated plastic also provides an aseptic container and, therefore, highly enhances sterility of the cyanoacrylate adhesive. As a result, the medical adhesive applicator requires less heat or irradiation to attain an FDA sterile approval. Such an aseptic applicator can also take advantage of the sterility method whereby the liquid adhesive can be sterile filtered and filled aseptically. By analogy, it is known by practitioners in the art, for example, that filling frangible glass vials with 2-octyl cyanoacrylate or formulated 2-octyl cyanoacrylate under a nitrogen blanket enhances the stability and sterility of glass vial, i.e., replacing non-sterile oxygen containing ambient air with inert, sterile nitrogen. Such processed filled vials have resulted in greater shelf life and require less radiation to achieve an FDA label as sterile. An inert gas blanket process in like manner applies to the applicators as illustrated in FIGS. 10-13.

In some preferred embodiments, discussed with regard to FIG. 14—FIG. 23, the tendency of initiator to be "washed out" as adhesive is pushed through an applicator head is addressed by using an applicator head that is sized to accommodate both the volume of adhesive and the associated volume of initiator. In such embodiments, the initiator is applied to and stored in the head within the interstitial spaces, e.g., of an open celled foam, cloth, or felt material. The adhesive is stored separately in an inert container. When used, the entire volume of adhesive is forced into the applicator head where it mixes uniformly with the initiator. When the mixture is applied, e.g., to seal a wound or to add a protecting layer, the mixture is uniform throughout the application. Such embodiments dispense adhesive that is mixed in the proper ratio from the start to the finish of the application. Thus, such embodiments avoid the "wash-out" effect of an initial rush of adhesive mixing with and depleting the available initiator to the extent that subsequent adhesive is not properly initiated and incompletely-cured "puddles" of adhesive are left on the application site.

Such embodiments may employ a squeezable, fluorinated polymer or plastic vial, as discussed previously, to provide storage stability. To use, the cap on said vial is removed by unscrewing or pulling, if it is a pressure fitted cap, and discarded. In its place, the vial is provided with an open cell foam head valve dispenser cap. In some embodiments, the foam may be replaced with a fabric or other porous or fibrous pad, such as felt. When the vial thusly equipped is inverted, squeezing the vial causes liquid to flow into the dispensing pad, allowing the fluid to be loaded into the foam head where it fully mixes with the initiator or accelerator that resides in the interstices and surfaces of the open cell foam. When the initiated sealant, protective coating, or wound adhesive is applied to skin or an incision wound it is uniformly mixed and, consequently, uniformly initiated and as a result cures uniformly. Also, unlike glass ampoule applicators, in the third embodiment the applicator parts may be recyclable.

Generally, embodiments in which glass is not used as the vial material have the advantages of two years or more of storage stability, an increased number of vial volume choices (vials from a few milliliters to several milliliters), a decrease in manufacturing complexity associated with not using plastic-sleeved glass ampoules, and the elimination of safety concerns related to glass shards. Furthermore, embodiments that employ a porous pad to receive the entire adhesive volume and allow it to mix with the initiator within the pad have the advantages of providing a uniformly initiated/accelerated adhesive/sealant, the elimination of hard porous tips/wafers/and silicon nozzle components, and the potential for a feather-light transfer of adhesive to the application surface—the lightness of transfer being provided by the flexibility of the pad, in contrast to rigid applicator tips.

The embodiments described within may be used for applying an adhesive or sealant discussed above. In some cases, the application may be a medical application. In some cases, the application may provide a covering or protective layer of sealant or adhesive. In some cases, the application may be to edges of a material, which are then brought together and joined, or the application may be topical to skin incision wounds after they have been approximated, which allows the wound edges to knit heal naturally.

Figure 14:
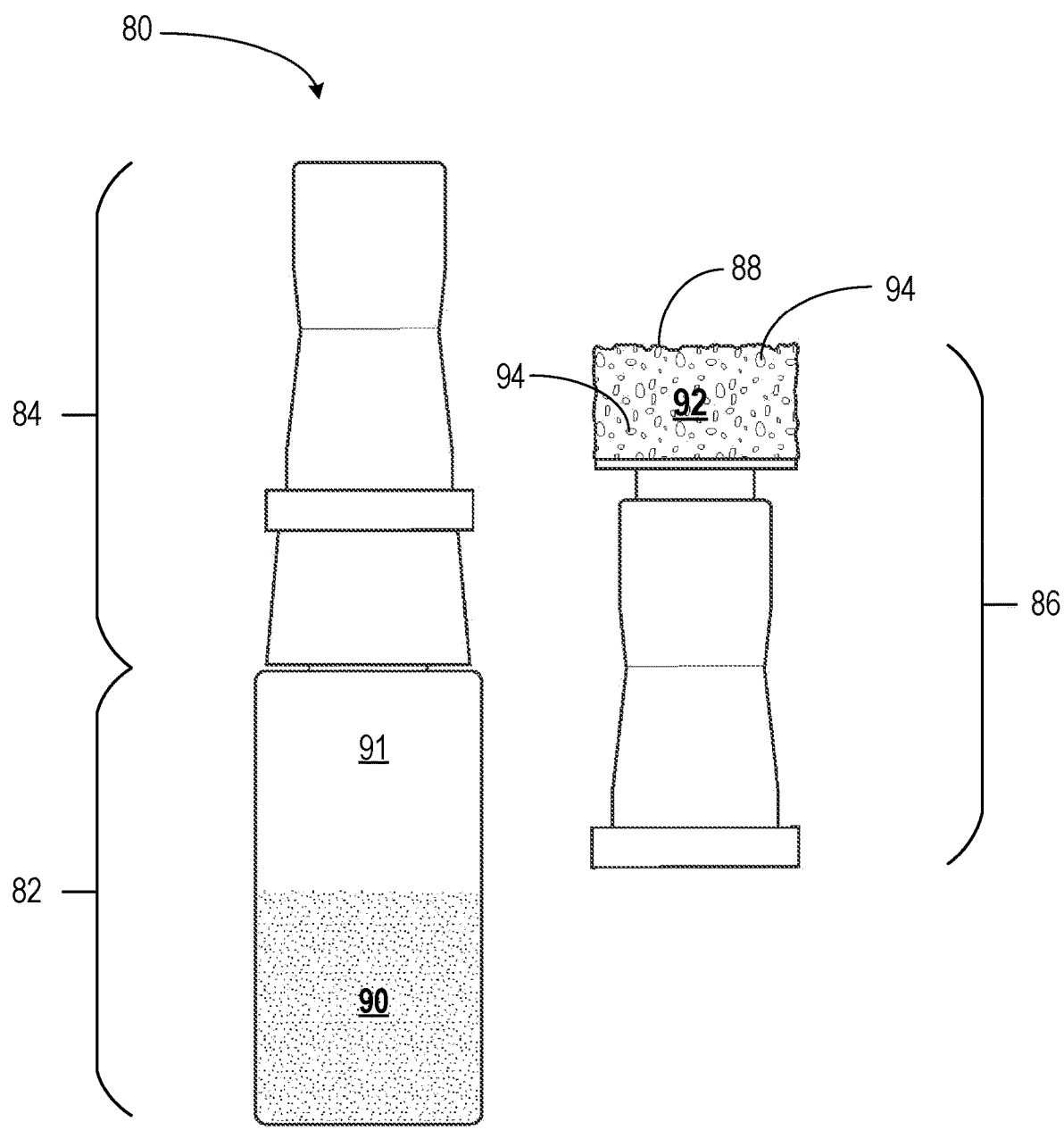
FIG. 14 is a side view illustrating an embodiment of an applicator of adhesive.

FIG. 14 is a side view illustrating an embodiment of an applicator 80 of an adhesive 90. In FIG. 14, applicator 80 includes a squeeze-able vial 82, a cap 84, and an applicator head 86. Vial 82 is provided with an adhesive 90 and a gas 91, which in the embodiment is an inert gas, such as argon. Applicator head 86 includes a porous pad 88 with pores or interstitial spaces 94. An initiator 92 is provided within pores 94.

In the embodiment, vial 82 may be a fluorinated polymer vial, which provides an environment that ensures the storage stability of an adhesive or sealant. The polymer material in the embodiment is flexible, allowing vial 92 to be squeezed to dispense adhesive 90. The relative volumes of adhesive 90 and initiator 92 may be determined according to manufacturer specifications for the adhesive. Given a determined total volume of adhesive 90 and initiator 92, pad 88 is sized so that at least the total volume may be retained within interstices 94. Initiator 92 is provided within interstices 94 of pad 88 in advance of the use of the applicator. Methods for introducing initiator 92 into pad 88 are known to those of skill and include dissolving or diluting an initiator in a solvent, such as acetone, and introducing an amount of the solution into pad 88 sufficient to leave the desired amount of initiator once the solvent has evaporated. Thus, the volume of material of pad 88 may be determined by the total volume of initiator 92 and adhesive 90, and the absorbent ability of the chosen pad material per unit volume. In the embodiment of FIG. 14, pad 88 is shown as an open cell foam. However, pads of other absorbent materials are envisioned, such as cloth or felt pads.

Initiator 92, being provided in an open cell foam or other porous material, may be a substance that is stable in such a material and when exposed to air. Such initiators and accelerators may be found as solids, liquids (e.g., an amine such as tryptamine), and potentially gels. However, if a desired initiator or accelerator is not stable when exposed to air, applicator head 86 may itself be encased in a protective layer, e.g., a cap, which must be removed in advance of using the applicator.

Figure 15:
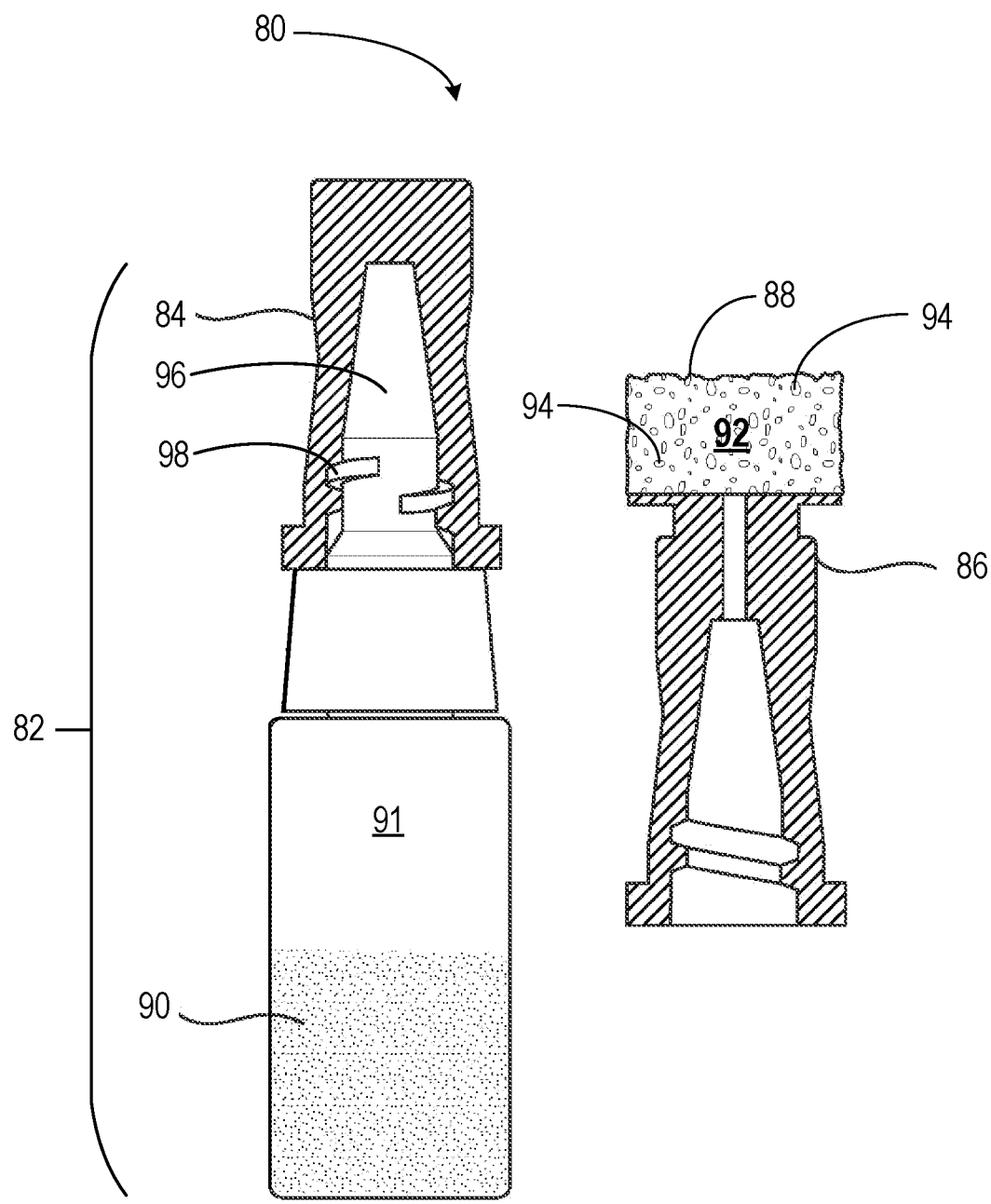
FIG. 15 is a cross-sectional view illustrating elements of the embodiment of FIG. 14.
Figure 16:
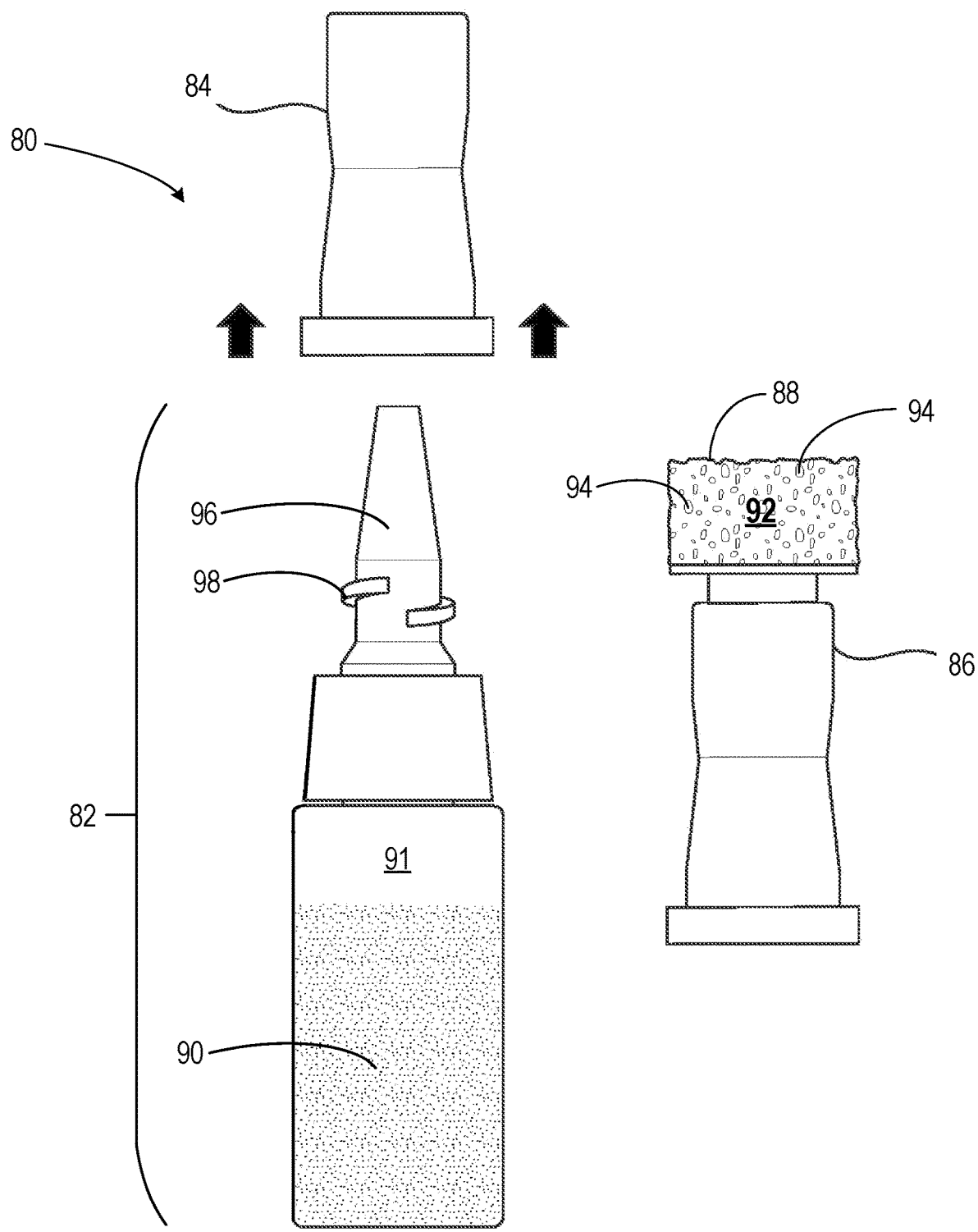
FIG. 16 is a side view illustrating aspects of the embodiment of FIG. 14.
Figure 17:
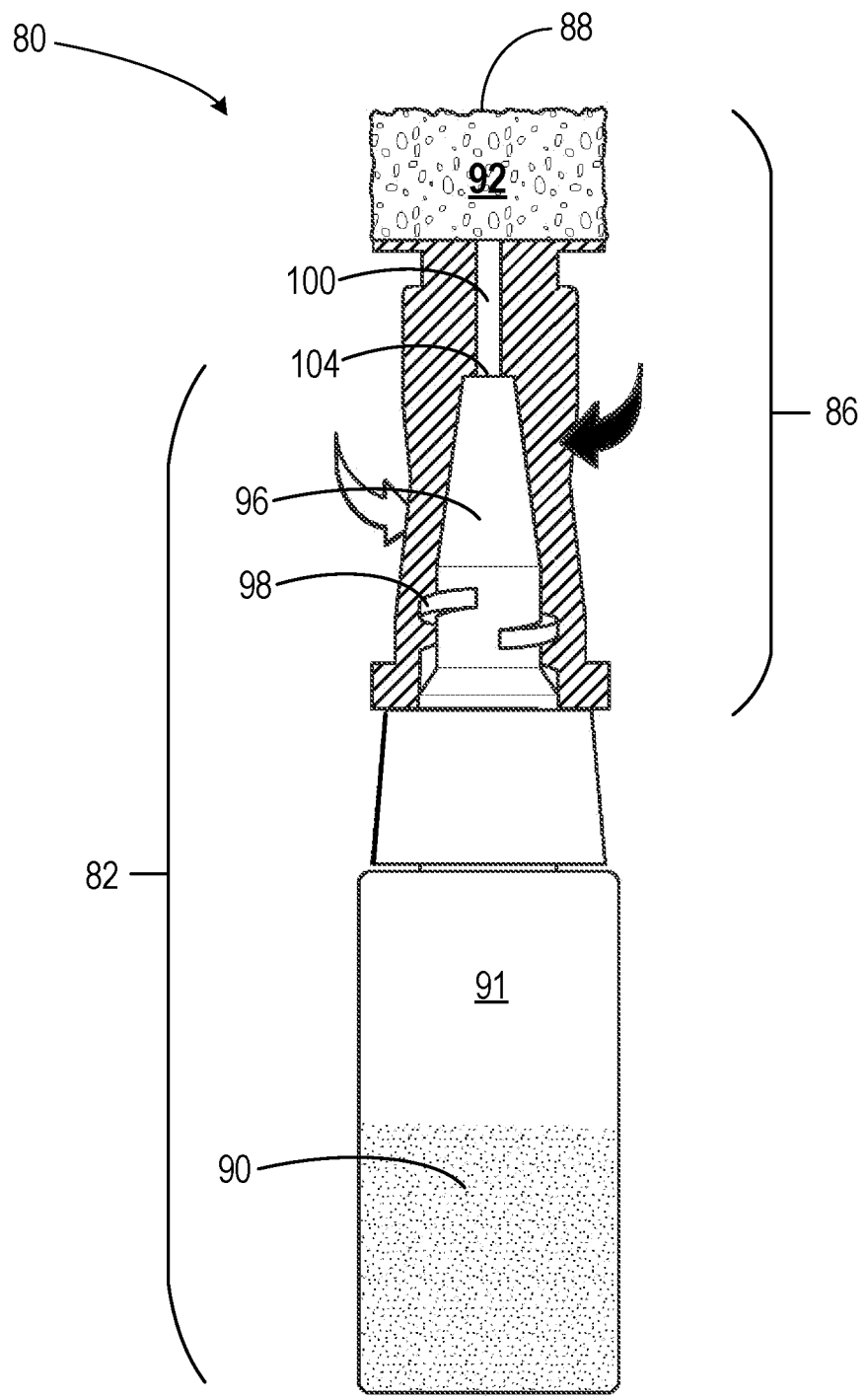
FIG. 17 is a cross-sectional view illustrating aspects of the embodiment of FIG. 14.

FIG. 15 is a cross-sectional view illustrating elements of applicator 80. In FIG. 15, cap 84 is shown in cross-section to reveal a nozzle 96 of vial 82. Nozzle 96 is threaded 98 to retain cap 84. Applicator head 86 is shown in cross-section to reveal a lumen 100 through which adhesive 100 may flow into pad 88. Applicator head 86 is similarly threaded 102 to cooperate with threads 98 in attaching head 86 to vial 82. In FIG. 16, cap 84 is removed to reveal nozzle 96, upon which applicator head 86 may now be mounted. In FIG. 17, applicator head 86 is shown mounted to vial 82. A nozzle hole 104 is provided in nozzle 96 to allow adhesive 90 to flow into lumen 100 and then into pad 88 to mix with initiator 92.

Figure 18:
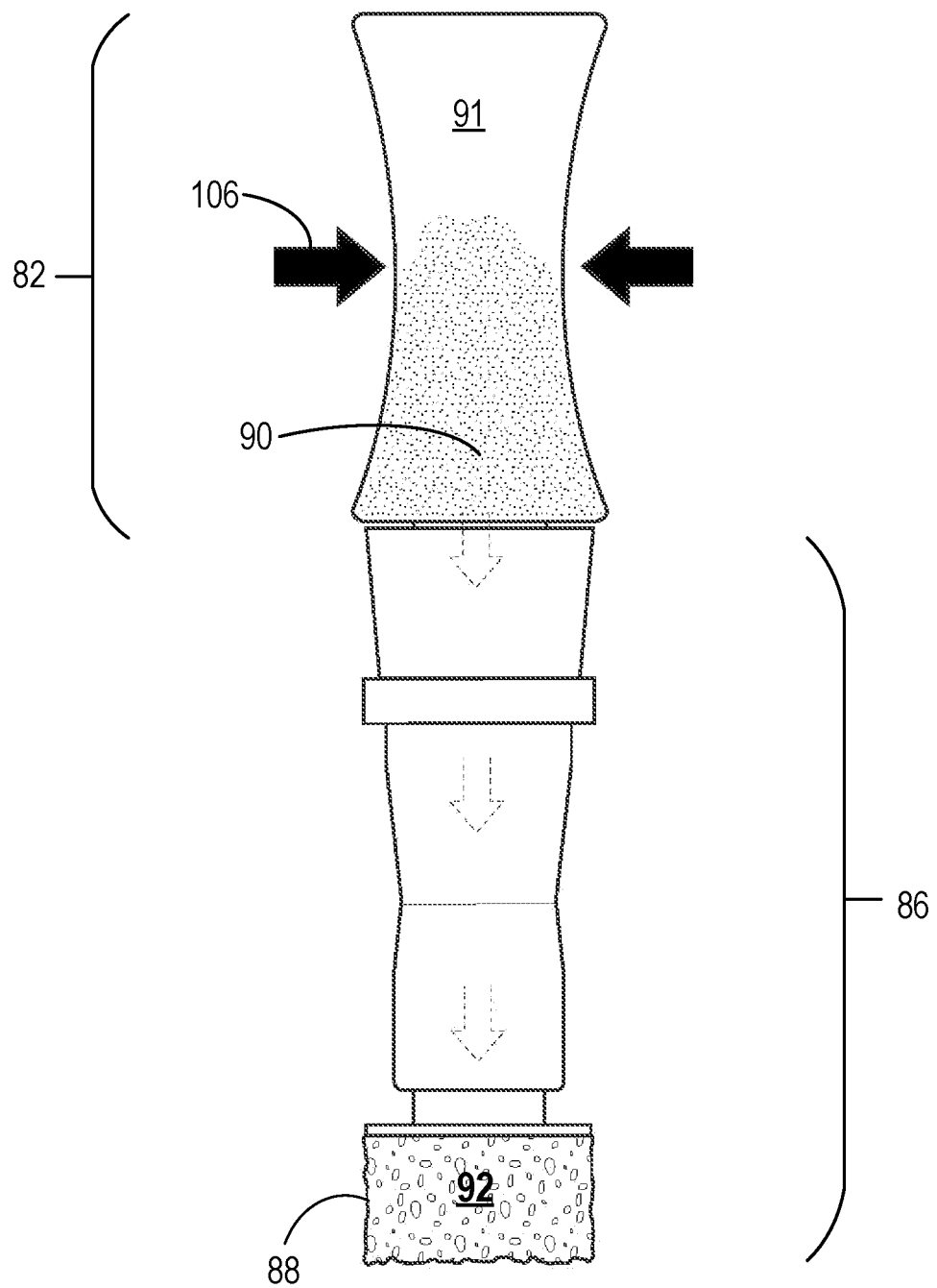
FIG. 18 is a side view illustrating aspects of the embodiment of FIG. 14.
Figure 19:
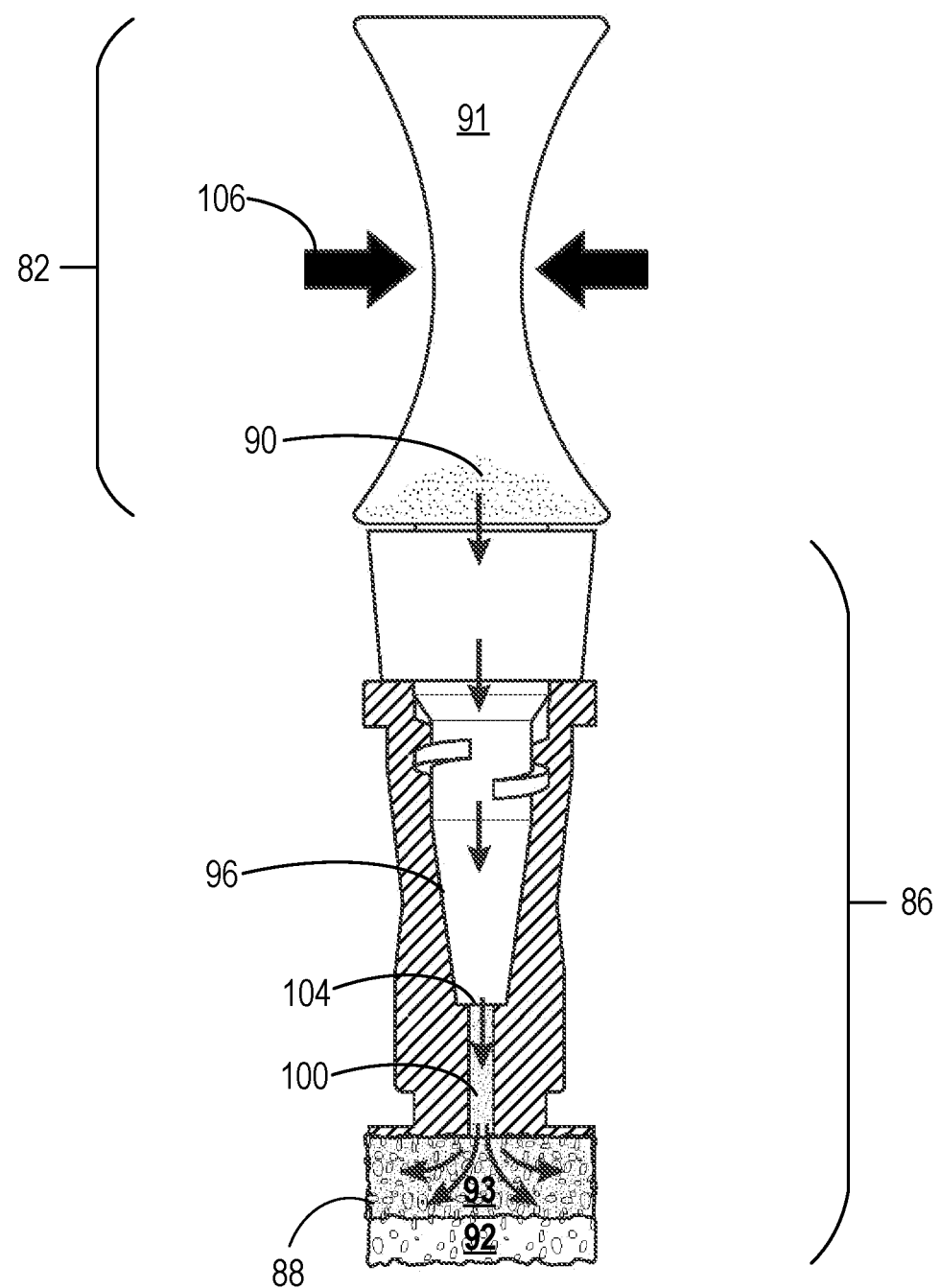
FIG. 19 is a cross-sectional view illustrating aspects of the embodiment of FIG. 14.

FIG. 18 is a side view illustrating aspects of applicator 80. In FIG. 18, applicator 80 has been inverted for application of adhesive 90. Upon applying a compressive force 106, adhesive 90 is forced from vial 82, through nozzle 104 and lumen 100, into pad 88 of applicator head 86. In FIG. 19, applicator head 86 is shown in cross-section to reveal the flow of adhesive 90 into pad 88. Adhesive 90, upon flowing into pad 88, mixes with initiator 92 to create an initiated mixture 93. Since some adhesive 90 is still retained within vial 82, the mixing of adhesive 90 and initiator 92 is not yet complete in FIG. 19.

Figure 20:
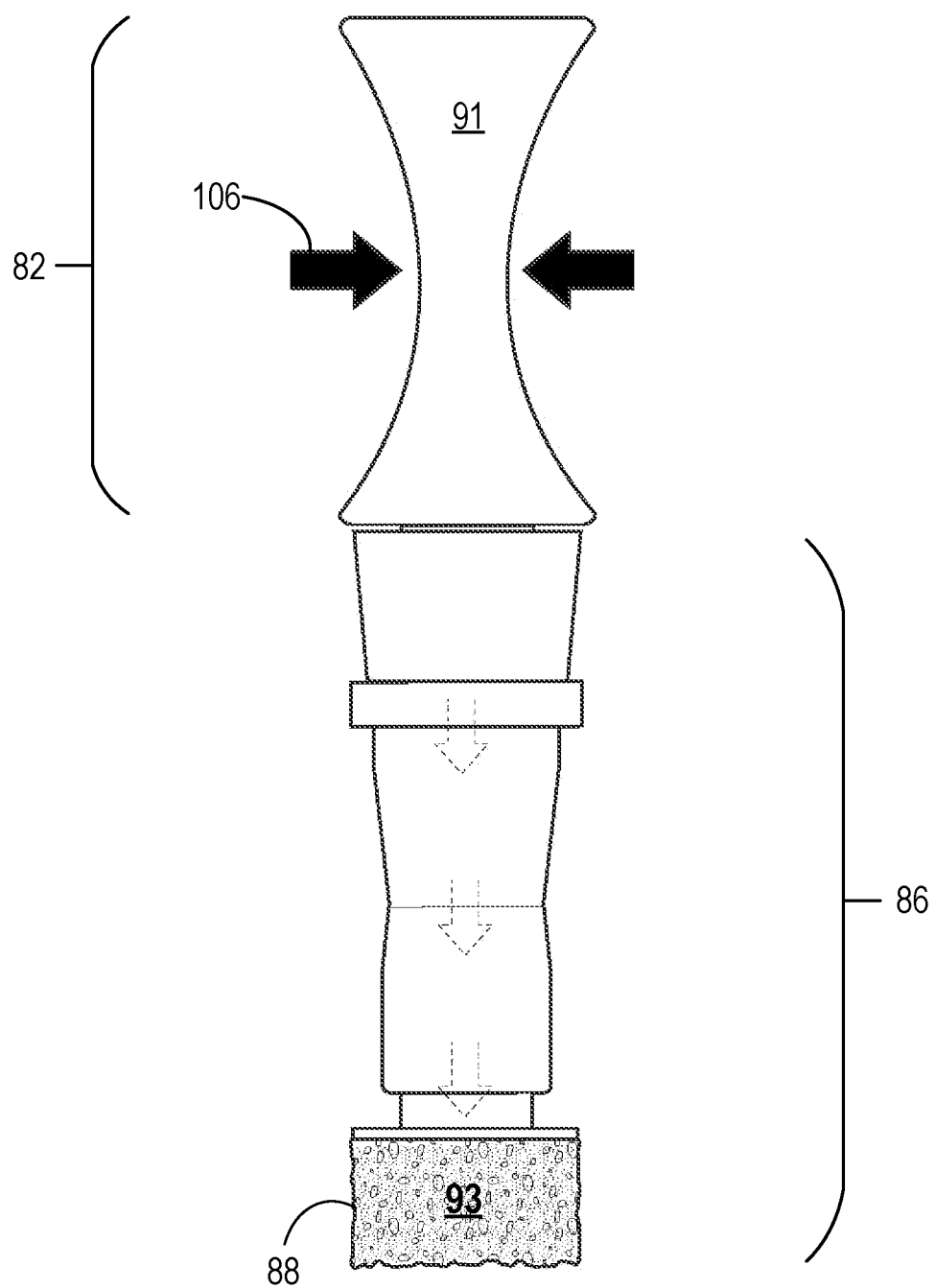
FIG. 20 is a side view illustrating aspects of the embodiment of FIG. 14.

In FIG. 20, adhesive 90 has been forced completely from vial 82 and into pad 88. FIG. 20 illustrates the advantage provided by sizing pad 88 to accommodate the entire volume of both adhesive 90 and initiator 92, namely, that mixture 93 is uniform. Thus, when mixture 93 is applied to a surface, the application will not suffer from puddles due to an improper adhesive/initiator ratio at some point of an application. In the embodiment, compressive force 106 may be applied gradually to allow adhesive 90 to mix with initiator 92 without being forced out of pad 88. However, force 107 need not be applied continuously, since if released, air may be sucked through pad 88 and into vial 82. Such a reverse flow may take with it some of mixture 93. However, any air within the vial may subsequently be used to force any remaining adhesive 90 or mixture 93 from the vial into pad 88 in the same manner as gas 107 is used.

Figure 21:
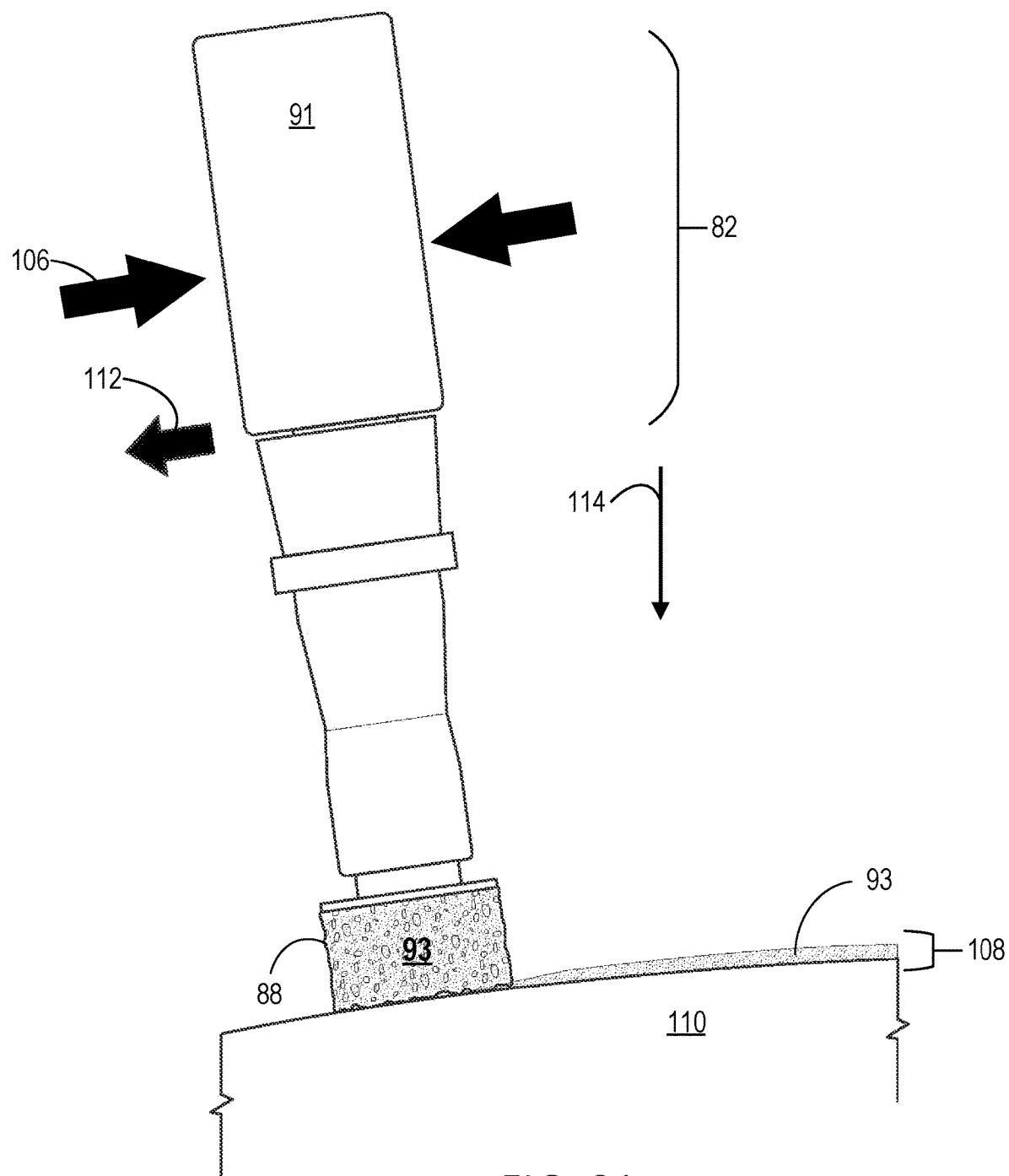
FIG. 21 is a side view illustrating the use of the embodiment of FIG. 14.

FIG. 21 is a side view illustrating aspects of the use of applicator 80. In FIG. 21, pad 88 has been brought into contact with a substrate 110, e.g., a patient's skin, and a layer 108 of mixture 93 applied. An amount of applied force 114 may be adjusted by the user to control the thickness of layer 108 as applicator 80 is moved across substrate 110 in a direction 112. In the embodiment, vial 82 may be squeezed 106, or not, as needed to ensure that no mixture 93 remains within nozzle 96. Force 114 may be modulated during application to control the amount of mixture 93 dispensed.

Figure 22:
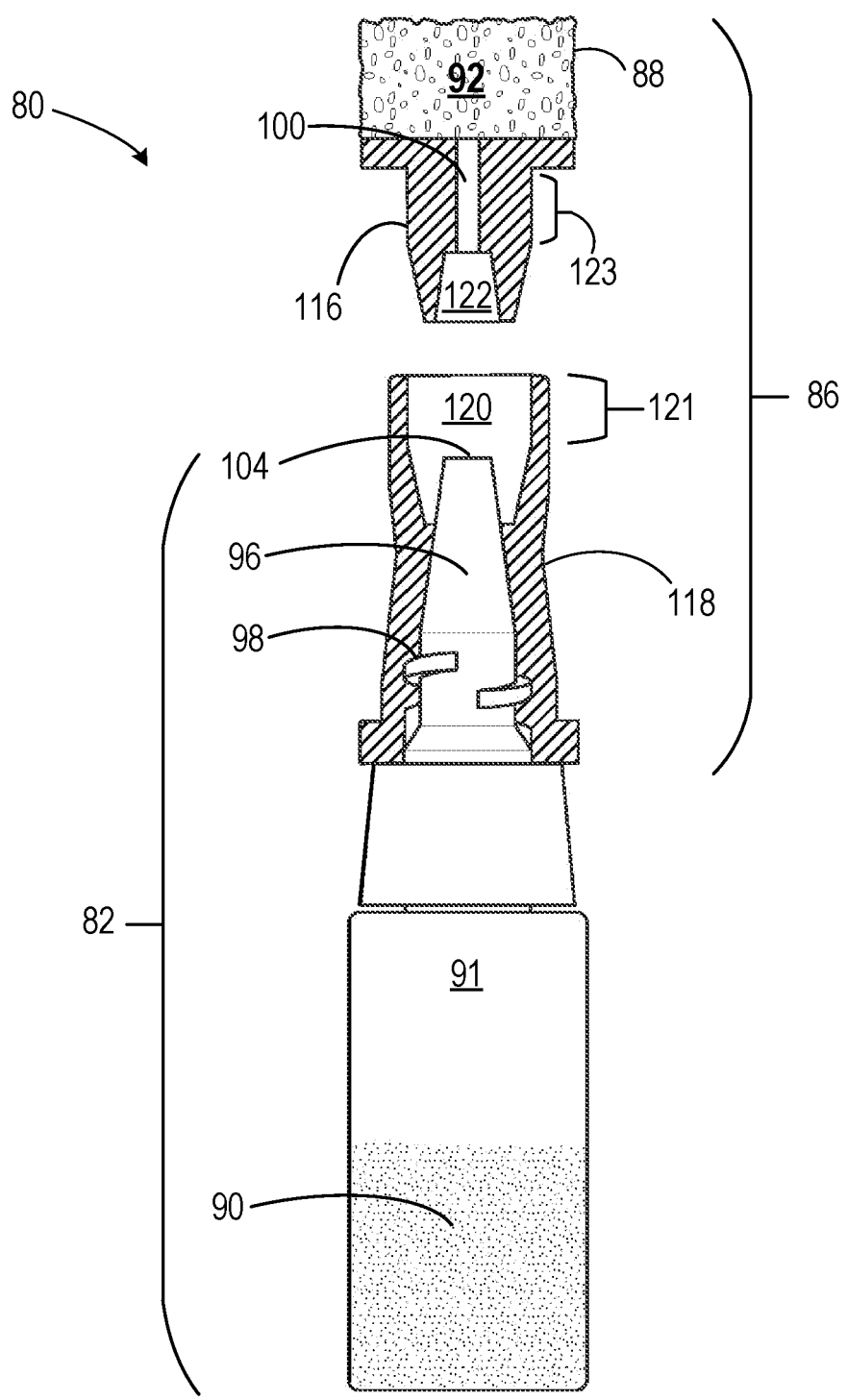
FIG. 22 is a cross-sectional side view illustrating an embodiment of an applicator of adhesive.

FIG. 22 is a cross-sectional side view illustrating an embodiment of applicator head 86. In FIG. 22, applicator head 86 is constructed of an upper piece 116 press fit into a lower piece 118. In the assembly, the tip of nozzle 96 is received by a conical cavity 122. Similarly, upper piece 116 is received within cavity 120, with the press fit obtained by the contact between sections 121 and 123.

Figure 23:
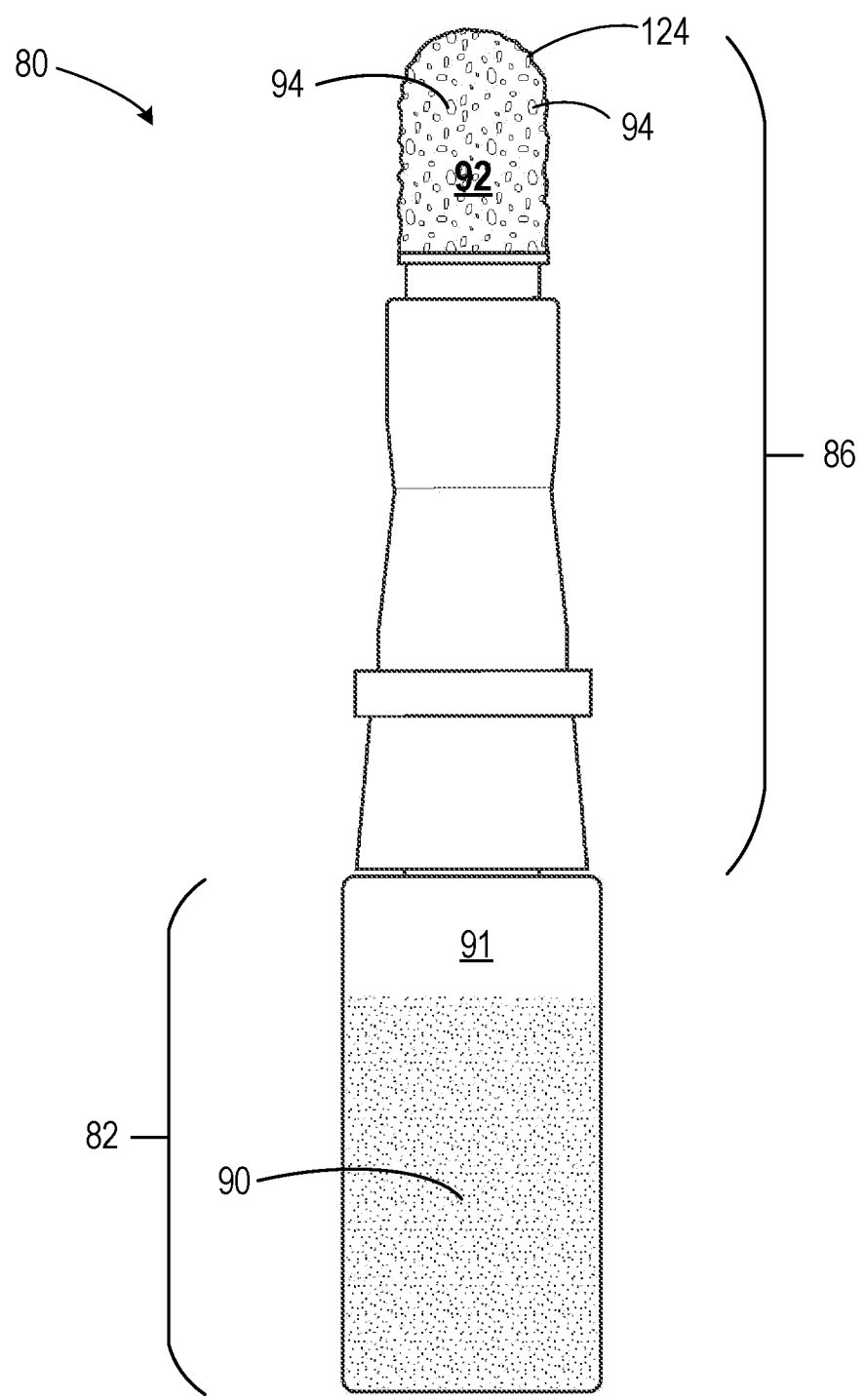
FIG. 23 is a side view illustrating an embodiment of an applicator of adhesive.

FIG. 23 is a side view illustrating an embodiment of applicator head 86. FIG. 23 illustrates that applicator head 86 may be provided with a pad 124 that has a geometry that is different from pad 88. In fact, applicator head 86 may be provided with a pad of any desired geometry, e.g., a geometry that may be suited for a particular task. Such geometries may include, e.g., a hemisphere, cylinder, a cone, a cube, or a triangular prism. Pad 124, which has a hemispherical upper surface, is suited for wound closure applications. In contrast, pad 88, which is cylindrical, is suited for applying a sealing or protective layer of adhesive to a surface. For example, the application of such a protective layer of a medical adhesive to injured skin may protect the injured skin from further injury. In particular, it is envisioned that application of a protective medical adhesive layer to a type 1, 2, or 3 pressure ulcer may be sufficient to prevent such a pressure ulcer from worsening, e.g., to a type 4 or 5 pressure ulcer.

Figure 24:
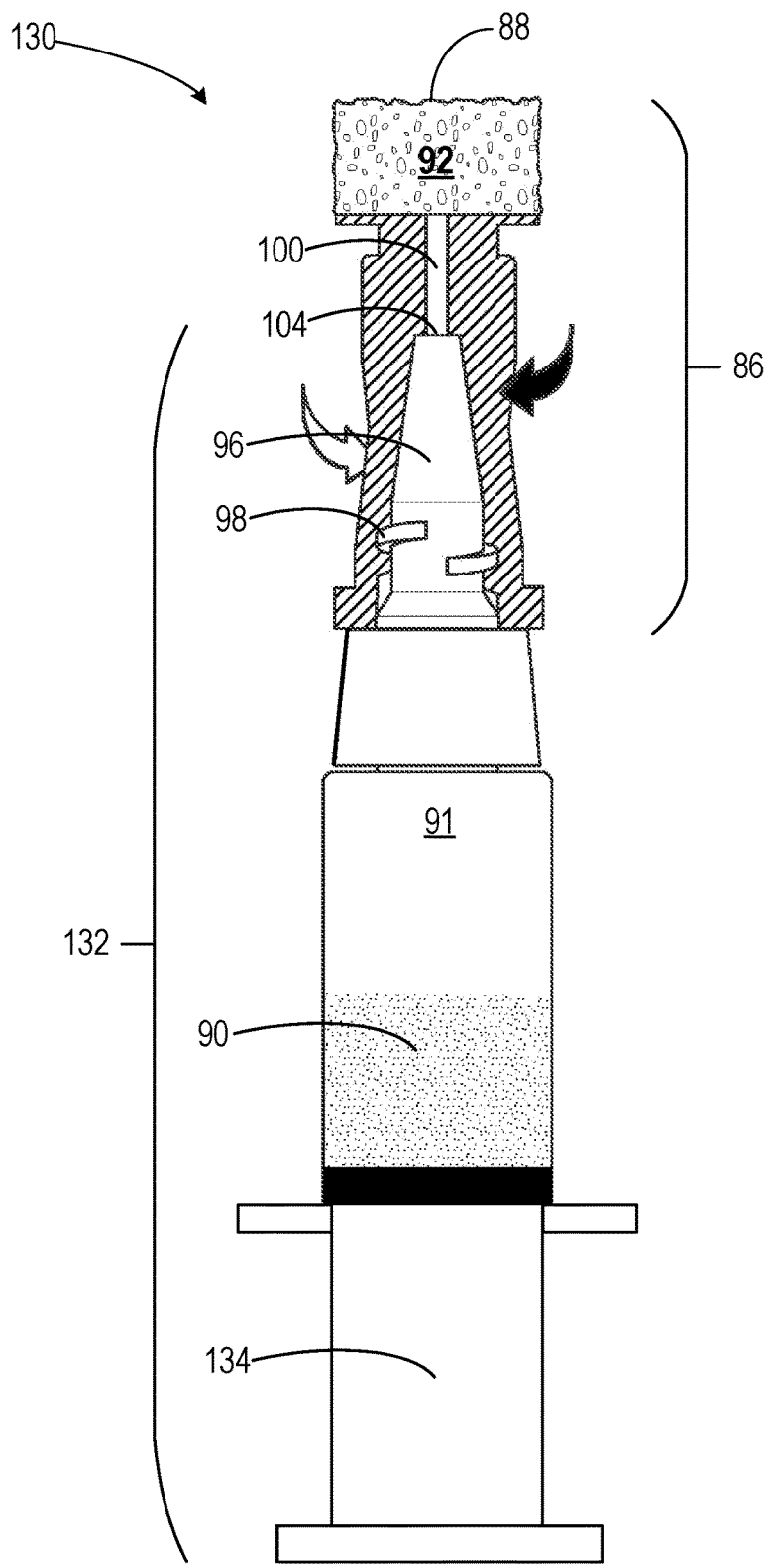
FIG. 24 is a side view illustrating an embodiment of an applicator of adhesive.

FIG. 24 is a side view illustrating an embodiment of an applicator 130 of adhesive. In FIG. 24, the squeeze-able vial has been replaced with a syringe 132 including a plunger 134. To mix, syringe 132 is uncapped (not shown) and connected to head 86. Plunger 134 is then depressed. Thus, the body of syringe 132 may be rigid. Except for the use of a plunger to force adhesive into pad 88, applicator 130 may be otherwise similar to applicator 80 and subsequent operation is as described with regard to FIG. 14-FIG. 23.

Generally, in this disclosure, discussion directed to "adhesive" is equally applicable to "sealant" and discussion directed to "initiator" is equally applicable to "accelerator." As such, disclosure directed to one or the other of adhesive or sealant, or of initiator or accelerator, should be understood to be applicable to both adhesive and sealant, or initiator and accelerator. Furthermore, the foam head may at time be discussed using the word "valve." However, the foam or otherwise porous pad and associated structure does not contain a "valve" in the sense of a one-way flapper or ball valve. Rather, the structure is discussed as being a valve in the sense that the porous pad hinders the passage of the adhesive from the vial. In this way, the valve aspect of the structure may also be considered a restriction in the flow path.

EXAMPLES

Example 1

Rate and Consistency of Medical Adhesive Dispensation Using Current DERMABOND® Applicator Experiments were performed to compare the rate and consistency of medical adhesive dispensation using current and legacy DERMABOND® applicators as compared with modified versions of those applicators based upon the principles of the present invention. In the first experiment, a current DERMABOND® DNX12 applicator (Lot LAJ279) filled with 0.70 ml of viscous 2-octyl cyanoacrylate adhesive was used. The current DERMABOND® DNX12 applicator has a longitudinal hole or lumen in its tip and a porous wafer above its tip similar to the embodiment shown in FIG. 4 of the present application. The objective of the experiment was to start flow quickly, preferably on the first squeeze, and dispense at a uniform rate of 0.025 grams per squeeze. TABLE 1 illustrates the measured flows for each squeeze of the DERMABOND® DNX12 plastic enclosure starting when the frangible glass vial was broken by the first squeeze of the plastic enclosure. For all the experiments, the amount of medical adhesive flow was measured by a JDS20 digital milligram scale manufactured by SmartWeight™ of New York, N.Y.

TABLE 1

| Squeeze | Weight of Dispensed Adhesive (grams) |
| --- | --- |
| 1 | 0 |
| 2 | 0.069 g |
| 3 | 0.025 g |
| 4 | 0.067 g |
| 5 | 0.050 g |
| 6 | 0.022 g |
| 7 | 0.042 g |
| 8 | 0.020 g |
| 9 | 0.025 g |
| 10 | 0.026 g |
| 11 | 0.028 g |
| 12 | 0.026 g (fully dispensed) |

The experimental results show that no medical adhesive was dispensed from the DERMABOND® DNX12 applicator on the first squeeze. On the second squeeze, a much higher amount of medical adhesive (0.069 grams) was dispensed than desired (0.025 grams). The amount of adhesive dispensed during the remaining squeezes continued to be erratic and all had undesirable, problematic bubbles.

Example 2

Rate and Consistency of Medical Adhesive Dispensation Using Modified Version of Current DERMABOND® Applicator For the second experiment, the DERMABOND® DNX12 applicator with viscous 2-octyl cyanoacrylate adhesive was modified in accordance with the principles of the present invention. Similar to the embodiment of the present invention shown in FIG. 4, an aperture was formed at the proximal end of the plastic enclosure and a squeeze tube of the type shown in FIG. 3 (without a one-way valve) was then compression fitted over the plastic enclosure. Again, the objective of the experiment was to start flow quickly, preferably on the first squeeze, and dispense at a uniform rate of 0.025 grams per squeeze. TABLE 2 illustrates the measured flows for each squeeze of the DERMABOND® DNX12 plastic enclosure starting when the frangible glass vial was broken by the first squeeze of the plastic enclosure.

TABLE 2

| Squeeze | Weight of Dispensed Adhesive (grams) |
| --- | --- |
| 1 | 0.046 g |
| 2 | 0.026 g |
| 3 | 0.026 g |
| 4 | 0.026 g |
| 5 | 0.027 g |
| 6 | 0.025 g |
| 7 | 0.024 g |
| 8 | 0.026 g |
| 9 | 0.023 g |
| 10 | 0.023 g |
| 11 | 0.023 g |
| 12 | 0.022 g |
| 13 | 0.035 g |
| 14 | 0.027 g (fully dispensed) |

The experimental results show that, as desired, medical adhesive was dispensed from the modified DERMA- BOND® DNX12 applicator on the first squeeze, albeit in a somewhat higher amount than desired. On the following squeezes, medical adhesive was dispensed from the modified DERMABOND® DNX12 applicator in a very consistent manner and free of bubbles with very little deviation from the desired 0.025 gram rate. This experiment shows that viscous medical adhesive can be easily and consistently dispensed using a medical adhesive applicator constructed in accordance with the principles of the present invention.

Example 3

Figure 1:
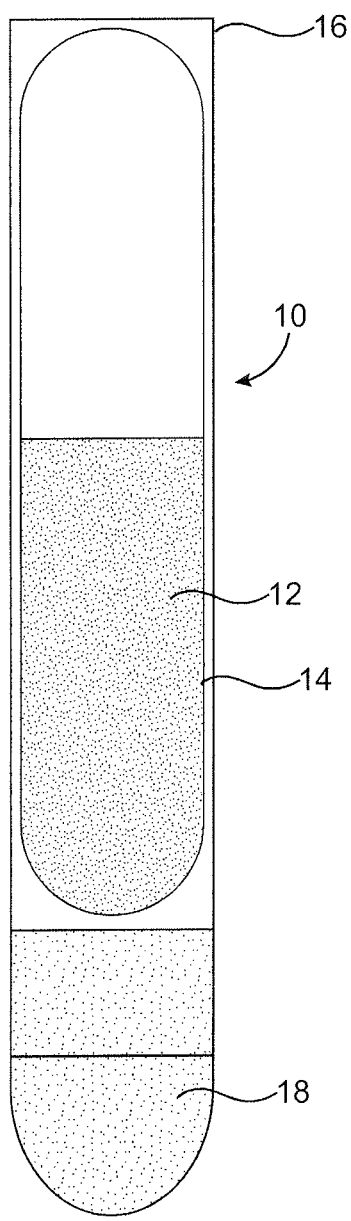
FIG. 1 illustrates a conventional, DERMABOND®-style frangible glass medical adhesive applicator.

Rate and Consistency of Medical Adhesive Dispensation Using a Legacy DERMABOND®-Style Applicator In the third experiment, an older DERMABOND® applicator with viscous 2-octyl cyanoacrylate adhesive as shown in FIG. 1 was recreated (since it is no longer commercially available). This legacy DERMABOND® applicator has a porous plug in its tip as shown in FIG. 1. Because the porous plug tip naturally yields a larger liquid expression than the lumen tip configuration, the objective of the experiment was to start flow quickly, preferably on the first squeeze, and dispense at a uniform rate of 0.033 grams per squeeze. It would be considered to be an acceptable and consistent rate of flow for the porous plug tip if one could control the flow to a range of 0.030 to 0.0360 grams per squeeze. TABLE 3 illustrates the measured flows for each squeeze of the legacy DERMABOND® plastic enclosure starting when the frangible glass vial was broken by the first squeeze.

TABLE 3

| Squeeze | Weight of Dispensed Adhesive (grams) |
| --- | --- |
| 1 | 0 |
| 2 | 0 |
| 3 | 0 |
| 4 | 0 |
| 5 | 0.035 g |
| 6 | 0.088 g |
| 7 | 0.059 g |
| 8 | 0.031 g |
| 9 | 0.025 g |
| 10 | 0.011 g (fully dispensed) |

The experimental results show that no medical adhesive was dispensed from the DERMABOND® applicator until the fifth squeeze. This may help explain why the legacy DERMABOND® applicator is no longer commercially available. After adhesive began flowing on the fifth squeeze, the amount of adhesive dispensed from squeeze to squeeze was highly erratic.

Example 4

Rate and Consistency of Medical Adhesive Dispensation Using Modified Version of a Legacy DERMABOND®-Style Applicator For the fourth experiment, a recreated legacy DERMABOND® applicator with viscous 2-octyl cyanoacrylate adhesive was modified in accordance with the principles of the present invention. Similar to the embodiment of the present invention shown in FIG. 4, an aperture was formed at the proximal end of the plastic enclosure and a squeeze tube of the type shown in FIG. 3 (without a one-way valve) was then compression fitted over the plastic enclosure. Because a porous plug tip was used, the objective of the experiment was again to start flow quickly, preferably on the first squeeze, and dispense at a uniform rate of 0.033 grams per squeeze. TABLE 4 illustrates the measured flows for each squeeze of the recreated legacy DERMABOND® plastic enclosure starting when the frangible glass vial was broken by the first squeeze of the plastic enclosure.

TABLE 4

| Squeeze | Weight of Dispensed Adhesive (grams) |
| --- | --- |
| 1 | 0.054 g |
| 2 | 0.031 g |
| 3 | 0.058 g |
| 4 | 0.036 g |
| 5 | 0.031 g |
| 6 | 0.033 g |
| 7 | 0.033 g |
| 8 | 0 (fully dispensed) |

The experimental results show that, with a modification based upon the present invention, medical adhesive was dispensed from the modified legacy DERMABOND® starting with the first squeeze. The amounts dispensed on each squeeze were generally within the acceptable range for a porous plug tip (i.e., 0.030 to 0.036 grams) and were consistent compared with the unmodified legacy DERMABOND® applicator. This experiment shows that a difficult and unreliable DERMABOND® medical adhesive applicator can be made reliable and relatively easy to use if it is modified in accordance with the principles of the present invention.

In the foregoing specification, the invention has been described with reference to specific preferred embodiments and methods. It will, however, be evident to those of skill in the art that various modifications and changes may be made without departing from the broader spirit and scope of the invention as set forth in the appended claims. For example, those of skill in the art will readily appreciate that a variety of materials may be used in making the applicators and applicator tips of the present invention and that those applicators and applicator tips may be made in a variety of dimensions. Moreover, while the focus of the specification has been on medical adhesives, those of skill in the art will recognize that other fluids can be advantageously used in the applicators of the present invention, including other medicaments, cosmetics, cleansing agents, surgical scrubs, paints, other adhesives, sealants, and the like. The specification and drawings are, accordingly, to be regarded in an illustrative, rather than restrictive sense, the invention being limited only by the appended claims.

The previous description is provided to enable any person skilled in the art to practice the various aspects described herein. In the embodiments, the separation of various system components in the embodiments described above should not be understood as requiring such separation in all embodiments. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more." Unless specifically stated otherwise, the term "some" refers to one or more. Headings and subheadings, if any, are used for convenience only and do not limit the subject disclosure.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as a "configuration" does not imply that such configuration is essential to the subject technology or that such configuration applies to all configurations of the subject technology. A disclosure relating to a configuration may apply to all configurations, or one or more configurations. A phrase such as a configuration may refer to one or more configurations and vice versa.

All structural and functional equivalents to the elements of the various aspects described throughout this disclosure that are known or later come to be known to those of ordinary skill in the art are expressly incorporated herein by reference and are intended to be encompassed by the claims.

What is claimed is:

1. A fluid applicator comprising:
an enclosure including a first aperture;
a volume of a fluid contained within the enclosure; and
a pad including a substance, the pad being porous, flexible, and connectable to the enclosure such that the fluid may pass through the first aperture and into the pad, wherein:
the pad is configured to absorb the entire volume of fluid in addition to the substance such that when the pad is connected to the enclosure and the entire volume of fluid is forced through the first aperture into the pad, the pad absorbs the entire volume of fluid providing for the entire volume of fluid and substance to mix within the pad to a target ratio before an application is begun.

2. The fluid applicator of claim 1, wherein, when the pad is connected to the enclosure and the fluid is forced through the first aperture into the pad and the pad absorbs the entire volume of fluid providing for the fluid and substance to mix, the mixture of fluid and substance at the target ratio is uniform and an application of the mixture cures without puddling.

3. The fluid applicator of claim 1, wherein the enclosure includes a squeeze-able vial and the fluid is forced through the first aperture by squeezing the vial.

4. The fluid applicator of claim 1, wherein the enclosure includes a plunger and the fluid is forced through the first aperture by pressing the plunger.

5. The fluid applicator of claim 1, wherein the pad includes an open-cell foam.

6. The fluid applicator of claim 1, wherein the pad includes a fabric or a felt.

7. The fluid applicator of claim 1, wherein the substance is a solid or a liquid.

8. The fluid applicator of claim 1, wherein the fluid is an adhesive or sealant and the substance is an accelerator or an initiator.

9. The fluid applicator of claim 8, wherein the adhesive or sealant is 2-octyl cyanoacrylate or formulated 2-octyl cyanoacrylate.

10. The fluid applicator of claim 8, wherein the substance is benzalkonium chloride (BAC).

11. The fluid applicator of claim 1, wherein the enclosure is comprised of a fluorinated plastic.

12. The fluid applicator of claim 1, wherein the pad is attached to a first cap including a second aperture and the first cap is connectable to the enclosure such that the fluid may pass through the first aperture, the second aperture, and into the pad.

13. The fluid applicator of claim 1, wherein the pad is a cylinder, a cone, or a triangular prism.

14. The fluid applicator of claim 1, wherein: the pad is configured to absorb the entire volume of fluid includes: the pad being sized such that the mixture of the entire volume of fluid and substance fills the pad.

15. A method for dispensing a fluid comprising:
selecting a fluid applicator having: an enclosure including a first aperture; a volume of a fluid contained within the enclosure; and a pad including a substance, the pad being porous, flexible, and connected to the enclosure such that the fluid may pass through the first aperture and into the pad, the pad being configured to absorb the entire volume of fluid in addition to the substance; and
forcing the entire volume of fluid through the first aperture and into the pad, the entire volume of fluid being absorbed by the pad to mix with the substance in a target ratio before an application is begun; and
applying the mixture of fluid and substance to a surface.

16. The method of claim 15, wherein the fluid is an adhesive or sealant and the substance is an accelerator or an initiator.

17. The method of claim 15, wherein the enclosure:
includes a squeeze-able vial and forcing the adhesive or sealant through the first aperture and into the pad includes squeezing the vial to force the adhesive or sealant through the first aperture; or
includes a plunger and forcing the adhesive or sealant through the first aperture and into the pad includes pressing the plunger to force the adhesive or sealant through the first aperture.

18. The method of claim 15, wherein the adhesive is 2-octyl cyanoacrylate or formulated 2-octyl cyanoacrylate and the substance is benzalkonium chloride.

19. The method of claim 15, wherein: the pad being configured to absorb the entire volume of fluid includes: the pad being sized such that the mixture of the entire volume of fluid and substance fills the pad.

20. A fluid applicator comprising:
an enclosure including a first aperture, the enclosure dimensioned to contain a volume of fluid; and
a pad including a substance, the pad being porous, flexible, and connected to the enclosure with a first aperture between the pad and enclosure, wherein:
the pad has absorbed the entire volume of fluid in addition to the substance such that the entire volume of fluid and substance have mixed within the pad to a target ratio.

* * * * *